（12） United States Patent
Thompson, III et al.

(10) Patent No.: US 7,902,218 B2
(45) Date of Patent: Mar. 8, 2011

(54) SUBSTITUTED TETRAHYDROISOQUINOLINES AS β-SECRETASE INHIBITORS

(75) Inventors: Lorin A. Thompson, III, Higganum, CT (US); Kenneth M. Boy, Durham, CT (US); Jianliang Shi, Hamdem, CT (US); John E. Macor, Guilford, CT (US); Andrew C. Good, Wallingford, CT (US); Lawrence R. Marcin, Bethany, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 627 days.

(21) Appl. No.: 11/951,516

(22) Filed: Dec. 6, 2007

(65) Prior Publication Data

US 2008/0153868 A1    Jun. 26, 2008

Related U.S. Application Data

(60) Provisional application No. 60/874,338, filed on Dec. 12, 2006.

(51) Int. Cl.
*C07D 217/00* (2006.01)
*A61K 31/47* (2006.01)
(52) U.S. Cl. .......... 514/300; 514/307; 546/113; 546/149
(58) Field of Classification Search .................. None
See application file for complete search history.

(56) References Cited

U.S. PATENT DOCUMENTS

2006/0046984 A1    3/2006    Thompson, III et al.

FOREIGN PATENT DOCUMENTS

| WO | WO 03/072535 | 9/2003 |
|---|---|---|
| WO | WO 2004/013098 | 2/2004 |
| WO | WO 2005/016876 | 2/2005 |

OTHER PUBLICATIONS

Luo, Yi, et al., "Mice deficient in BACE1, the Alzheimer's β-secretase, have normal phenotype and abolished β-amyloid generation", *Nature Neuroscience* 4 (2001) 231-232.

Roberds, S.L. et al., "BACE knockout mice are healthy despite lacking the primary β-secretase activity in brain: implications for Alzheimer's disease therapeutices", *Human Molecular Genetics* 10 (2001) 1317-1324.
Seiffert, D.; et al., "Presenilin-1 and -2 are molecular targets for γ-secretase inhibitors", *J. Biol. Chem.* 275 (2000) 34086-34091.
Selkoe, D. J., "Biochemical Analyses of Alzheimer's Brain Lesions lead to the Identification of αβ and its Precursor", *Ann. Rev. Cell Biol.* 10 (1994) 373-403.
Selkoe, D. J., "Alzheimer's Disease: Genes, Proteins, and Therapy", *Physiol. Rev.* 81 (2001) 741-766.
Sinha, S., et al., "Purification and cloning of amyloid precursor protein β-secretase from human brain", Nature 402 (1999) 537-540.
Thal, D.R., et al., "Two Types of Sporadic Cerebral Amyloid Angiopathy", J. Neuropath. Exp. Neuro. (2002) 61: 282-293.
Vassar, R., et al., "β-Secretase Cleavage of Alzheimer's Amyloid Precursor Protein by the Transmembrane Aspartic Protease BACE", Science 286 (1999) 735-741.
Wolfe, M. J., "Secretase Targets for Alzheimer's Disease: Identification and Therapeutic Potential", J. Med. Chem. 44 (2001) 2039-2060.
Yan, R., et al., "Membrane-anchored aspartyl protease with Alzheimer's disease β-secretase activity", Nature 402 (1999) 533-537.

*Primary Examiner* — Zinna N Davis
(74) *Attorney, Agent, or Firm* — John F. Levis; Aldo A. Algieri

(57) ABSTRACT

There is provided a series of tetrahydroisoquinoline diaminopropane compounds of Formula (I) or a stereoisomer; or a pharmaceutically acceptable salt thereof,

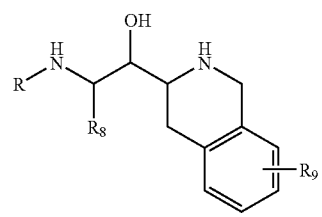

wherein R, $R_8$ and $R_9$ are as defined herein, their pharmaceutical compositions and methods of use. These compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

7 Claims, No Drawings

SUBSTITUTED TETRAHYDROISOQUINOLINES AS β-SECRETASE INHIBITORS

CROSS-REFERENCE TO RELATED APPLICATIONS

This is a non-provisional application which claims the benefit of U.S. Provisional Application No. 60/874,338 filed Dec. 12, 2006.

FIELD OF THE DISCLOSURE

This patent application provides substituted tetrahydroisoquinoline diaminopropane compounds having drug and bio-affecting properties, their pharmaceutical compositions and method of use. In particular, the disclosure is concerned with a series of substituted tetrahydroisoquinoline diaminopropanes which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.* 1994, 10, 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [Sinha, S., et al., *Nature* 1999, 402, 537-540; Vassar, R., et al., *Science* 1999, 286, 735-741; Yan, R. et al., *Nature* 1999, 402, 533-537].

Removal of BACE activity in mice by gene targeting completely abolishes Aβ production [see Luo, Y., et al., *Nature Neuroscience* 2001, 4, 231-232; Roberds, S. L., et al., *Human Molecular Genetics* 2001, 10, 1317-1324]. BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2004013098, published Feb. 12, 2004, discloses lactam derivatives as beta-secretase inhibitors.

PCT Publication WO 2003072535, published Sep. 4, 2003, discloses substituted hydroxyethylamines in the treatment of Alzheimer's Disease.

PCT Publication WO 2005016876, published Feb. 24, 2005. discloses cyclic amines having a benzamide substituent.

US Patent Application Publication No. US20060046984A1, published Mar. 2, 2006, to Thompson, et al., discloses gamma lactam compounds as beta-secretase inhibitors.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, pre-

SUMMARY OF THE DISCLOSURE

A series of substituted tetrahydroisoquinoline diaminopropane substituted tetrahydroisoquinolines having the Formula (I)

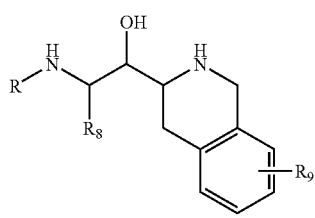

or a stereoisomer; or a pharmaceutically acceptable salt thereof, wherein $R_1$, $R_2$, and $R_3$, as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and nontoxic pharmaceutically acceptable salts thereof have the following formula and meanings:

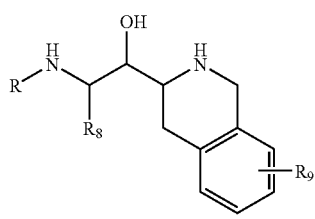

wherein
R is

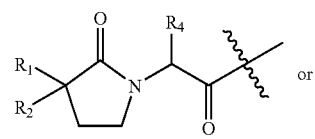

or

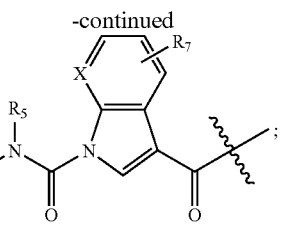

$R_1$ is hydrogen, $C_{1-6}$alkyl or $NHR_3$;
$R_2$ is $C_{1-6}$alkyl, $C_{3-6}$alkenyl, $C_{3-6}$cycloalkyl or $C_{3-6}$cycloalkyl($C_{1-4}$alkyl) in which each group is optionally substituted with a group selected from halogen, $CF_3$, $CF_2H$, OH, $OCF_3$ and $C_{1-4}$alkoxy;
$R_3$ is $-C(=O)R_{10}$, $-C(=O)OR_{10}$, $-C(=O)NHR_{10}$, $-S(O)_nR_{10}$ or $C_{1-6}$alkyl optionally substituted with a group selected from $C_{3-6}$cycloalkyl, halogen, $CF_3$, $OCF_3$, OH, $C_{1-4}$alkoxy and CN;
$R_4$ is $C_{1-6}$alkyl, $C_{3-6}$cycloalkyl, $C_{3-6}$cycloalkyl($C_{1-4}$alkyl), phenyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;
$R_5$ is H or $C_{1-6}$alkyl;
$R_6$ is H or $C_{1-6}$alkyl, or $R_5$ and $R_6$ together form a five or six-membered carbocyclic ring which can optionally be substituted with $C_{1-6}$alkyl or $CH_2OCH_3$;
$R_7$ is H, halogen, or $CF_3$;
$R_8$ is $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;
X is CH or N;
$R_9$ is OH, $C_{1-6}$alkoxy or $C_{1-6}$alkyl optionally substituted with halogen, OH, $CF_3$, $OCF_3$, or $C_{1-6}$ alkoxy; and
$R_{10}$ is $C_{1-4}$alkyl optionally substituted with the group selected from halogen, OH, $CF_3$, $NH_2$ and $C_{1-4}$alkoxy;
or a nontoxic pharmaceutically acceptable salt thereof.

The present application also provides a method for the treatment or alleviation of disorders associated with β-amyloid peptide, especially Alzheimer's Disease, cerebral amyloid angiopathy, inclusion body myositis and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Dingwall, C. *Journal of Clinical Investigation* 2001, 108, 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" and "$C_{1-10}$ alkyl" denotes alkyl having 1 to 6 or 1 to 10 carbon atoms. Examples of alkyl include, but are not limited to, methyl, ethyl, n-propyl, i-propyl, n-butyl, i-butyl, sec-butyl, t-butyl, pentyl, hexyl, octyl and decyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. An example of a preferred stereochemical configuration is the isomer:

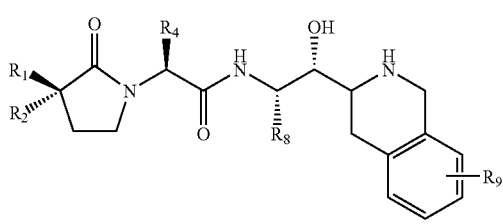

Ia or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Additionally, the carbon atom to which $R_1$ and $R_2$ is attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "nontoxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds of the present application may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, the tetrahydroisoquinoline diaminopropanes can be prepared by coupling, under standard conditions known to one skilled in the art, a substituted γ-lactam 2 and a substituted tetrahydroisoquinoline hydroxyethyl amine 3. Methods for the synthesis of γ-lactams 2 are known in the art and are disclosed in a number of references including but not limited to those given below. The synthesis of substituted tetrahydroisoquinoline diaminopropanes is disclosed in detail in the discussion given below.

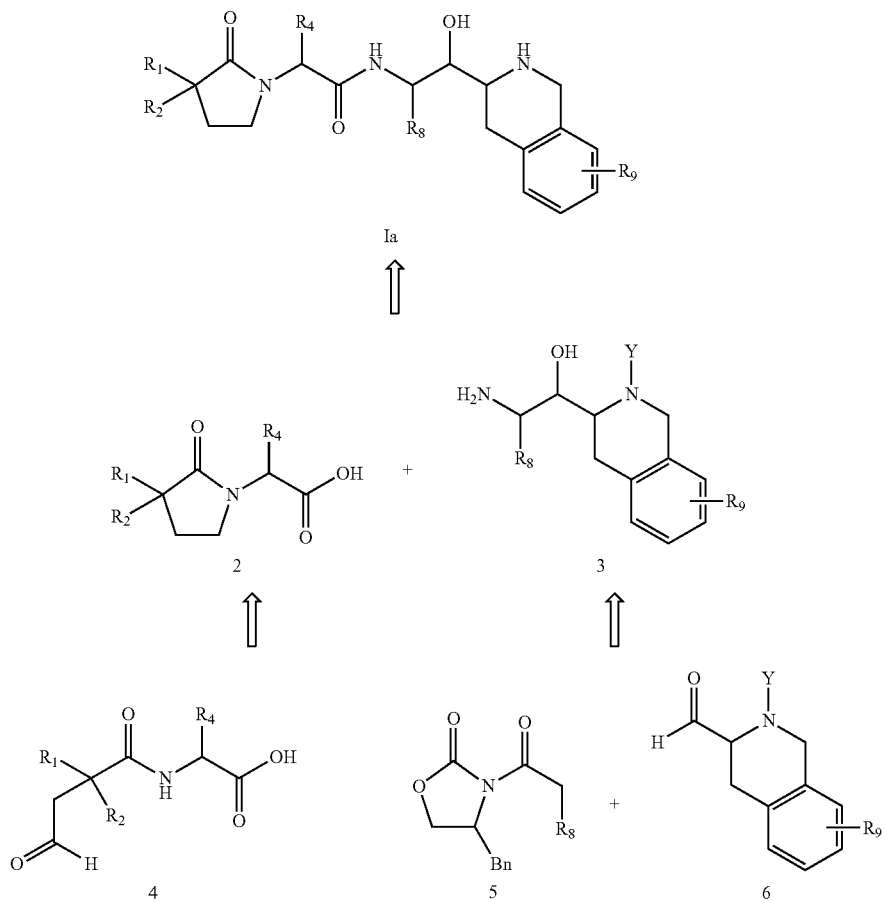

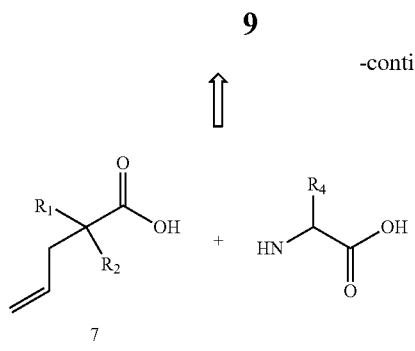

Y = H, Protecting Group

Compounds of the invention may also be synthesized by coupling a tetrahydroisoquinoline diaminopropane 3 with a functionalized indole carboxylic acid or 7-azaindole carboxylic acid 8 in the manner described in general reaction scheme B.

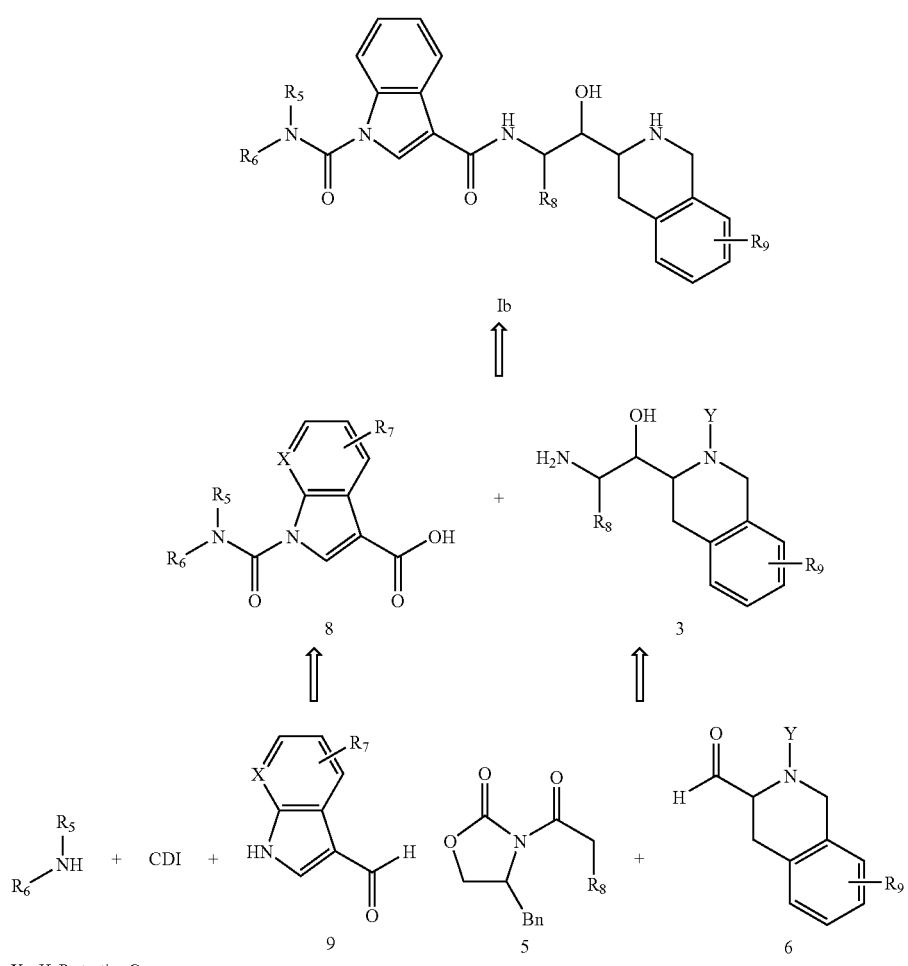

Y = H, Protecting Group
X = CH or N
CDI = carbonyldiimidazole

Description—General Reaction Scheme A

A preferred subset of lactams of formula 2 are represented by formula 2a and are known as

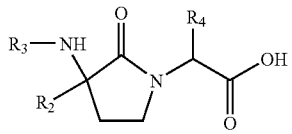

disubstituted γ-lactams. Disubstituted γ-lactams 2 can be prepared by cyclization of an aldehyde-containing dipeptide precursor 4 followed by deprotection of the amino group and functionalization with a suitable reaction partner, such as a carboxylic acid or an activated derivative thereof, a sulfonyl halide, isocyanate, or chloroformate. Alternatively, the amino group can be alkylated under standard conditions known to one skilled in the art, for example, using an aldehyde and a reducing agent such as sodium borohydride or derivatives thereof. The dipeptide precursor 4 is prepared by coupling a natural or unnatural amino acid ester to a quaternary α-allyl amino acid 7, followed by oxidation of the allyl group to the requisite aldehyde and cyclization. Substituted cyclic hydroxyethyl amines 3 are prepared using an aldol reaction of a cyclic aldehyde 6 with a functionalized enolate, followed by Curtius rearrangement of the resulting acid to the amine 3. Further details of the preparation of compounds are provided below.

Synthesis of a substituted quaternary α-allyl amino acid 7 is carried out according to one of several literature methods. Scheme 1 shows the method of Seebach, et. al., (Seebach, D.; Hoffmann, M. *European Journal of Organic Chemistry* 1998, 1337-1351, Hoffmann, M.; Blank, S.; Seebach, D.; Kusters, E.; Schmid, E. *Chirality* 1998, 10, 217-222, Hoffmann, M.; Seebach, D. *Chimia* 1997, 51, 90-92, Blank, S.; Seebach, D. *Angew. Chem.* 1993, 105, 1780-1781 (See also Angew. Chem., Int. Ed. Engl., 1993, 1732(1712), 1765-1786), where (R)- or (S)-tert-butyl 2-tert-butyl-4-methoxy-2,5-dihydro-1,3-imidazole-1-carboxylate 10 is alkylated sequentially with allyl iodide and a $R_1$-group electrophile (which can be suitably protected by one skilled in the art if necessary) to provide a protected amino acid equivalent with high diastereoselectivity.

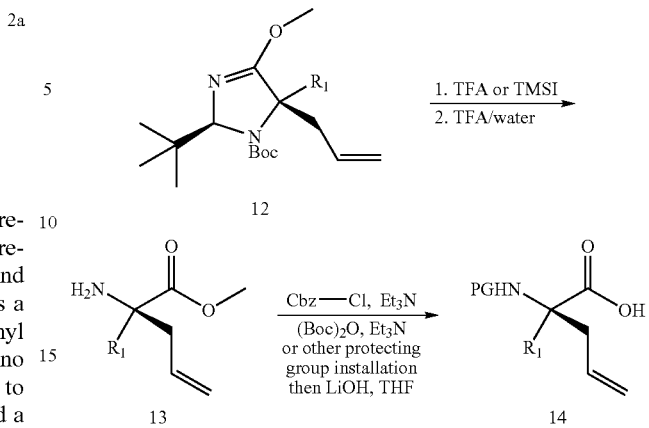

The scalemic amino acid is then generated by deprotection of the Boc group and acidic deprotection of the trimethylacetyl acetal. The resulting amino acid methyl ester 13 can then be protected under standard conditions with protecting groups (PG) well known to those skilled in the art, such as t-butyloxycarbonyl (Boc) or benzyloxycarbonyl (Cbz), and saponified to the free carboxylic acid 14.

Alternatively, quaternary amino acids can be synthesized from the corresponding amino acid (Scheme 2). Using isoleucine as an example, formation of the benzylidene imine followed by cyclization with benzyloxycarbonyl chloride provides a protected amino acid precursor 17 (Seebach, D.; Fadel, A. *Helv. Chim. Acta.* 1985, 68, 1243 and Altmann, E.; Nebel, K.; Mutter, M. *Helv. Chim, Acta* 1991, 74, 800; De, B.; Dellaria, J. F.; Baker, W. R.; Zydowsky, T. M.; Rosenberg, S. H. et al., EP 365992, 1990). Alkylation with allyl bromide or iodide provides the alkylated lactone 18 which can be deprotected under basic conditions to provide the protected amino acid derivative 19 which can be directly coupled as is shown in Scheme 2.

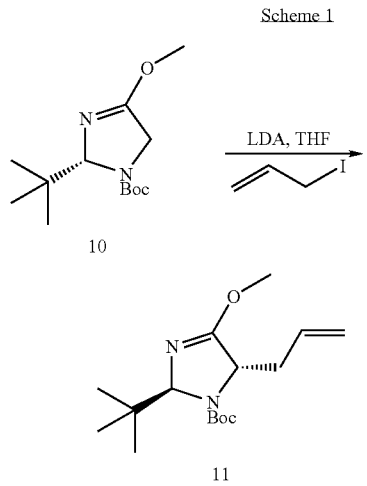

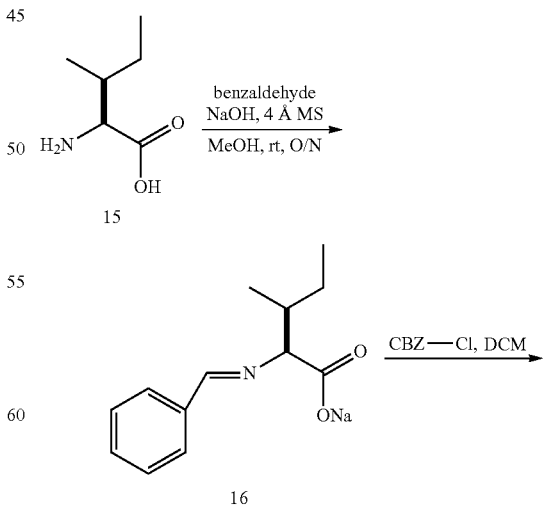

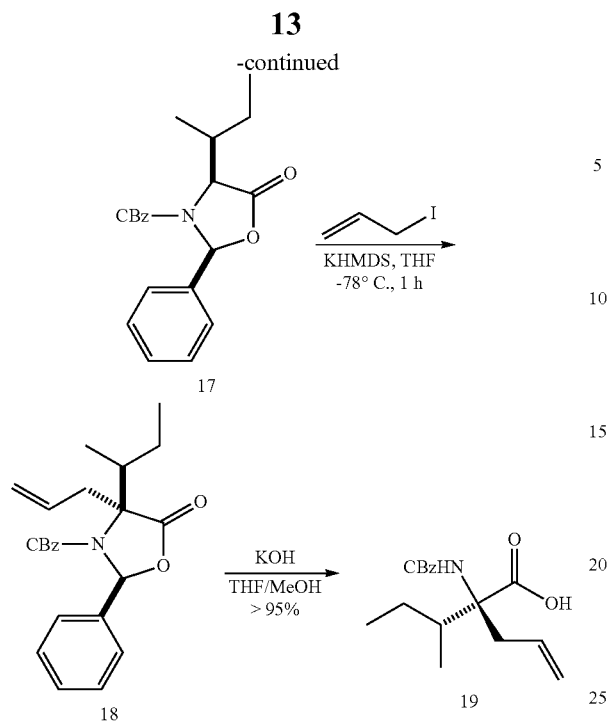

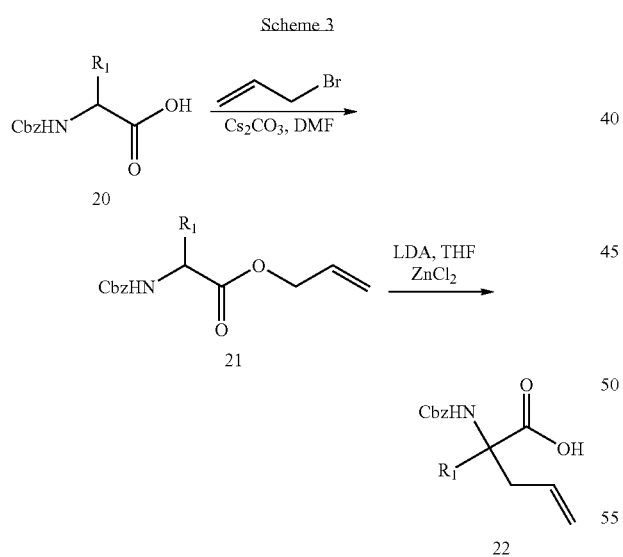

An additional method for the preparation of quaternary amino acids is shown in Scheme 3. Treatment of an amino acid 20 with allyl bromide in the present of Cs$_2$CO$_3$ provides the amino acid allylic ester 21. Ester enolate Claisen rearrangement of 21 results in 22 (Kazmaier, U. and Maier, S. *Tetrahedron* 1996, 52, 941).

Amino acids used as the starting materials in the chemistry reported herein can be natural or unnatural. Many are available as items of commerce in suitably protected form, or unprotected where protecting groups can be installed under standard conditions to one skilled in the art. Additional methods for the preparation of unnatural amino include the Strecker synthesis or amidomalonate synthesis. In addition, the Myers pseudoephedrine glycinamide alkylation method (Myers, A. G.; Gleason, J. L.; Yoon, T.; Kung, D. W. *J. Am. Chem. Soc.* 1997, 119, 656-673), Schollkopf stereoselective alkylation (Schollkoft, U.; Hartwig, W.; Groth, U. *Angew. Chem. Int. Ed. Engl.* 1979, 18, 863), and Evans electrophilic azidation (Evans, D. A.; Britton, T. C.; Ellman, J. A.; Dorow, R. L. *J. Am. Chem. Soc.* 1990, 112, 4011) may be used to prepare natural or unnatural amino acids in enantiomerically pure form.

A specific example of the production of substituted homophenylalanine derivatives related to compound 30 can be prepared using the chemistry shown in Scheme 4. Commercial Boc-aspartic acid benzyl ester can be reduced through the intermediate succinimide ester to produce the alcohol 25. Iodination followed by formation of the alkyl zinc iodide and Negishi-type coupling under palladium catalysis produces substituted, protected homophenylalanines 27 which can be deprotected in the standard manner using trifluoroacetic acid or HCl to produce indermediates 28, useful in the formation of substituted lactams of type 33.

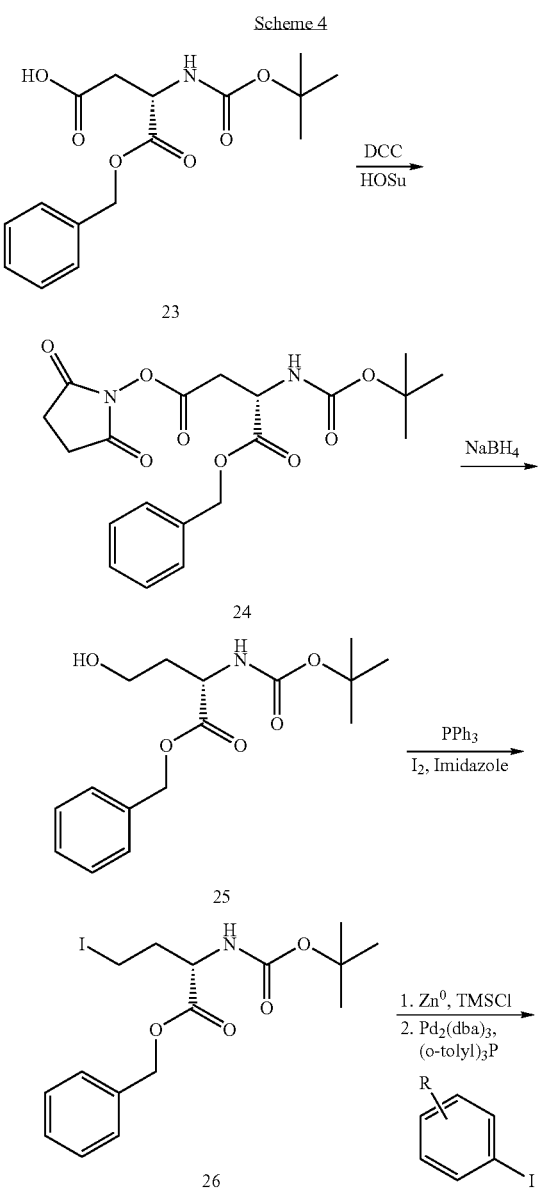

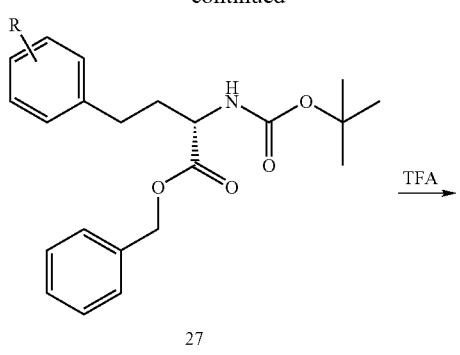

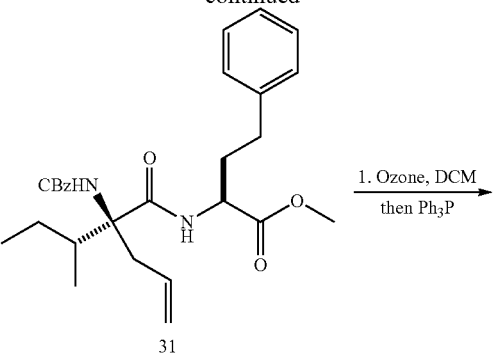

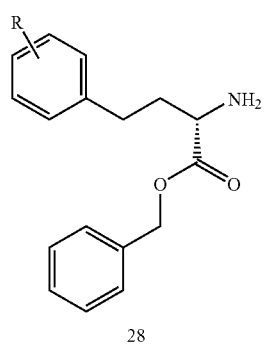

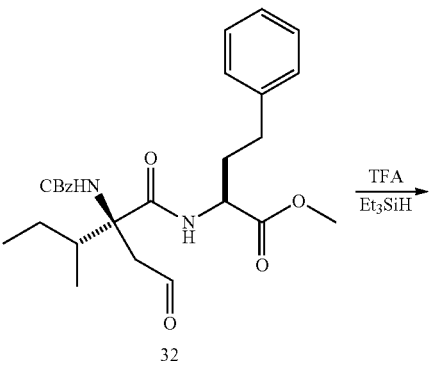

A quaternary amino acid 29 may then be coupled under standard conditions to a natural or unnatural amino acid ester using standard coupling reagents like HATU (O-(7-azabenzotriazol-1-yl)-1,1,3,3-tetramethyluronium hexafluorophosphate) or PyBOP (benzotriazole-1-yl-oxy-tris-pyrrolidino-phosphonium hexafluorophosphate) in the presence of a tertiary amine base such as triethylamine, N,N-diisopropylethylamine, or N-methylmorpholine (Scheme 5). Oxidation of the allyl group using oxonolysis or osmium tetroxide/sodium periodate gives the aldehyde which is cyclized to the γ-lactam 33 using triethylsilane and trifluoroacetic acid (Holladay, M. W.; Nadzan, A. M. *J. Org. Chem.* 1991, 56, 3900-3905; Duan, J. PCT International Publication WO 0059285, 2000.

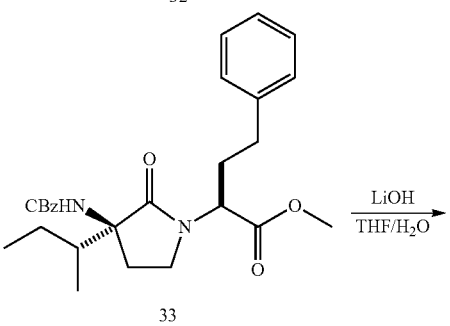

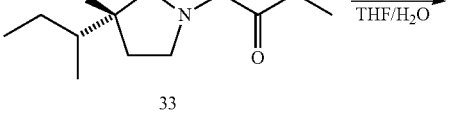

Scheme 5

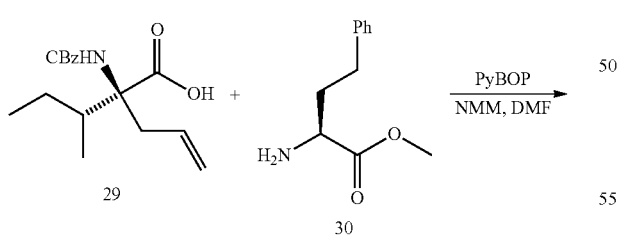

Cleavage of the amino acid ester using saponification conditions such as lithium or sodium hydroxide in aqueous solution provides the protected lactam 34 for coupling to the diaminopropane fragment.

Lactams may also be synthesized in the manner demonstrated in Scheme 6, where the quaternary amino acid is directly oxidized to the aldehyde, and a second amino acid ester is introduced by reductive alkylation using a reducing agent such as sodium borohydrode, sodium triacetoxyborohydride, or sodium cyanoborohydride to produce an amine 38. The product can then be cyclized directly to form the desired γ-lactam (see, for instance, Scheidt, K. A.; Roush, W. R.; McKerrow, J. H.; Selzer, P. M.; Hansell, E.; Rosenthal, P. J. *Bioorganic & Medicinal Chemistry* 1998, 6, 2477-2494.

Scheme 6

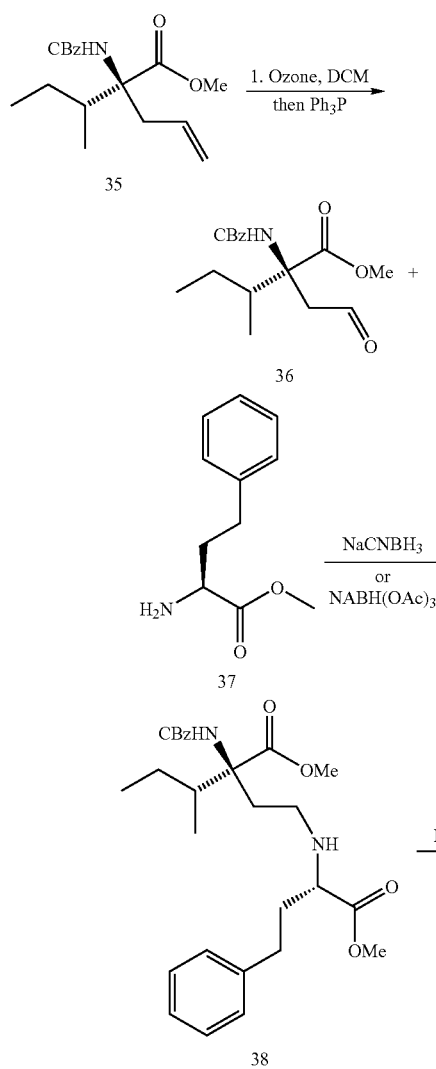

Scheme 7

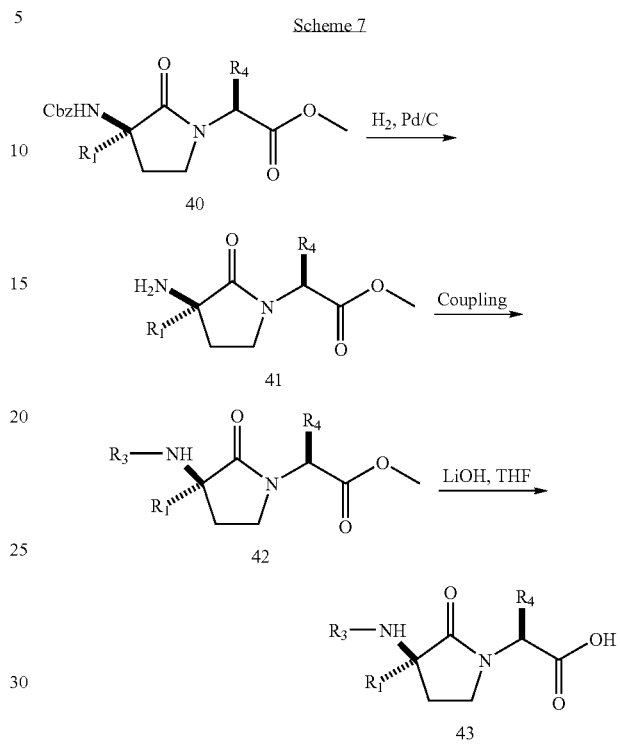

carboxylic acid 43 ready to couple to the cyclic diaminopropane fragment in protected or unprotected form.

The lactam amine protecting group may now be removed by catalytic hydrogenation or other suitable methods (Scheme 7), and the primary amine center may be further functionalized by reacting with agents such as carboxylic acids or their activated variants such as acid chlorides or acid anhydrides to make amides such as 42. A number of other derivatives 42 can be prepared, including but not limited to the reaction with sulfonic acids or sulfonyl halides to prepare sulfonamides, chloroformates to provide carbamates, or carbamoyl chlorides or isocyanates to provide ureas. Saponification of the methyl ester of these derivatives provides the Another preferred subset of lactams of formula 2 are represented by formula 49 (Scheme 8) and are known as monosubstituted γ-lactams. A variety of alpha-allyl carboxylic acids 46 are available utilizing known asymmetric alkylation methodology (for a review, see: Jones, S. *J. Chem. Soc. Perkins I* (2002), 1-21.). Evan's asymmetric alkylation methodology employing N-acycloxazolidinones has proven particularly useful to prepare these alpha-allyl acids [(a) Munoz, L. et. al. *J. Org. Chem.* (2001), 66, 4206. (b) Evans, D. A. et. al. *J. Org. Chem.* (1999), 64, 6411.], and the products so obtained can be reacted in a similar manner as the quaternary amino acids as outlined in Scheme 5 to form the appropriate lactams 49.

Scheme 8

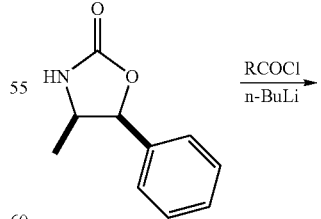

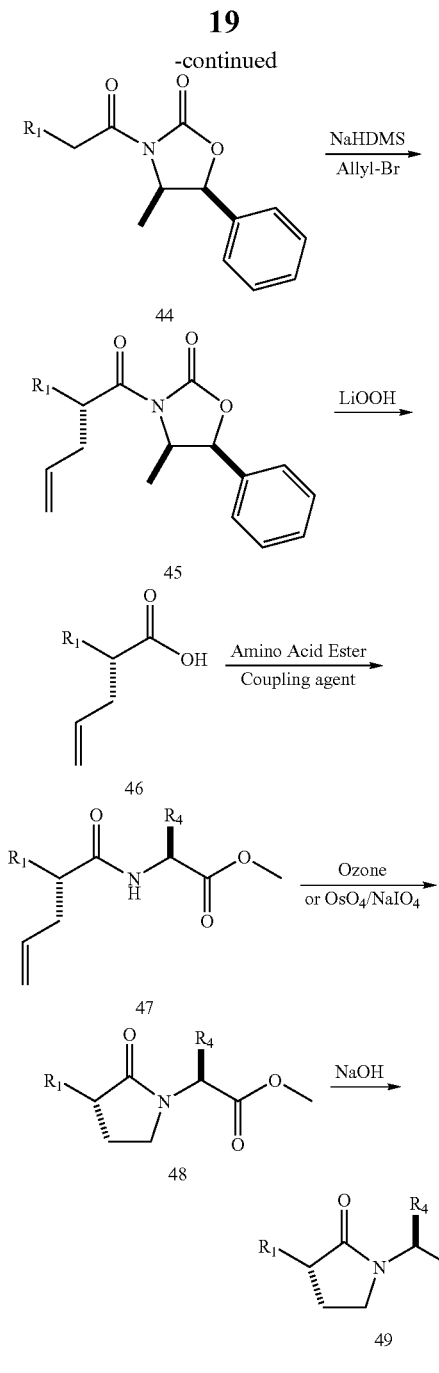

Scheme 9 discloses methods for preparing substituted tetrahydroisoquinoline hydroxyethyl amines of type 3 that are used as a coupling partner for lactam acids 2 or (aza)indole acids 8. The method relies on the diastereoselective aldol reaction of a suitable enolate equivalent with a substituted tetrahydroisoquinoline aldehyde. There are a number of methods for the diastereoselective aldol reaction, including those developed by Masamune, (See, for instance, Masamune, S.; Ali, S. A.; Snitman, D. L.; Garvey, D. S. Aldol condensation with increased stereoselectivity through use of an enantioselective chiral enolate. *Angewandte Chemie* 1980, 92, 573-575, and Masamune, S.; Choy, W.; Kerdesky Francis, A. J.; Imperiali, B. Stereoselective aldol condensation. Use of chiral boron enolates. *Journal of the American Chemical Society* 1981, 103, 1566-1568.) and Heathcock (See Heathcock, C. H. Acyclic stereoselection via the aldol condensation. *ACS Symposium Series* 1982, 185, 55-72., Pirrung, M. C.; Heathcock, C. H. Acyclic stereoselection. 8. A new class of reagents for the highly stereoselective preparation of threo-2-alkyl-3-hydroxycarboxylic acids by the aldol condensation. *Journal of Organic Chemistry* 1980, 45, 1727-1728.). The most commonly used method, and the one described herein, is the method of Evans, reported in a large number of articles including Gage, J. R.; Evans, D. A. Diastereoselective aldol condensation using a chiral oxazolidinone auxiliary. *Organic Syntheses* 1990, 68, 83-91.

Substituted tetrahydroisoquinoline aldehydes can be prepared by a number of methods. One of the more general methods is to prepare a substituted tetrahydroisoquinoline carboxylic acid via the Friedel-Crafts cyclization of a substituted phenylalanine derivative, commonly known as the Pictet-Spengler reaction, shown in Scheme 9, equation (1). In this method, a substituted phenylalanine derivative is condensed with an aldehyde under mild dehydrating conditions to form a Schiff base, or imine. Reagents used to effect transformation to the imine include magnesium sulfate, molecular sieves, or simple azeotropic distillation, and the like. The imine is them treated with an activating agent which induces Friedel-Crafts cyclization to the tetrahydroisoquinoline. Common activating agents include strong acids such as hydrochloric, phosphoric, sulfuric, trifluoromethanesulfonic, or trifluoroacetic acid and metal halides such as tin or aluminum chlorides. An alternative method is to acylate the phenylalanine derivative with a carboxylic acid derivative and an acylating agent, producing an amide (Scheme 9, equation 2). The amide thus produced is then cyclized to the tetrahydroisoquinoline under dehydrating conditions employing reagents including, but not limited to, phosphorus oxychloride, oxalyl chloride, and others. This process is known as the Bischler-Napieralski reaction (see Whaley, W. M.; Govindachari, T. R. *Org. React.* 1951, 6, 74).

Scheme 9

(1)

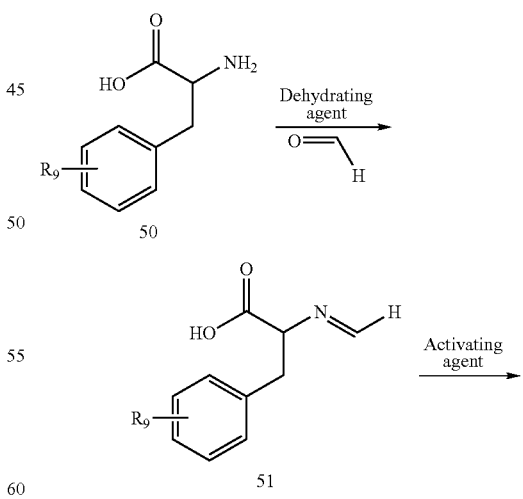

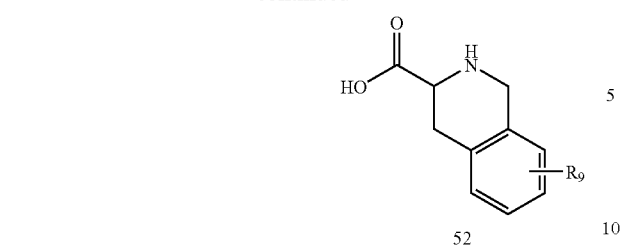

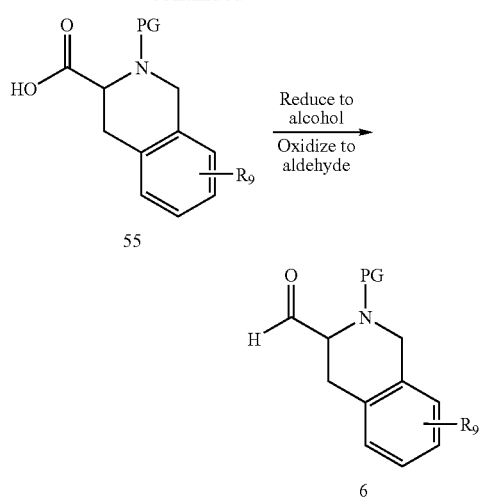

A method for preparing 7-substituted tetrahydroisoquinolines is shown in Scheme 11. Thus, bromination of commercially available m-tyrosine

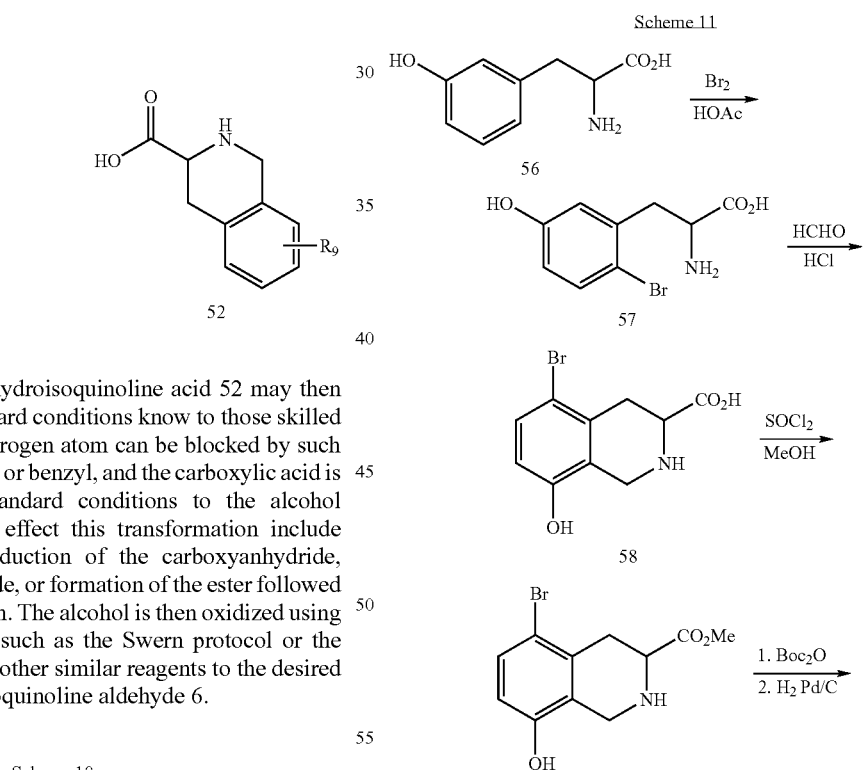

The substituted tetrahydroisoquinoline acid 52 may then be protected using standard conditions know to those skilled in the art. In general, nitrogen atom can be blocked by such protecting groups as Boc or benzyl, and the carboxylic acid is then reduced under standard conditions to the alcohol (Scheme 10). Ways to effect this transformation include sodium borohydride reduction of the carboxyanhydride, lithium aluminum hydride, or formation of the ester followed by borohydride reduction. The alcohol is then oxidized using a mild oxidizing agent such as the Swern protocol or the Dess-Mertin reagent, or other similar reagents to the desired substituted tetrahydroisoquinoline aldehyde 6.

Scheme 10

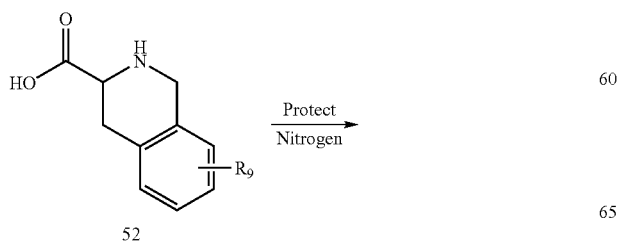

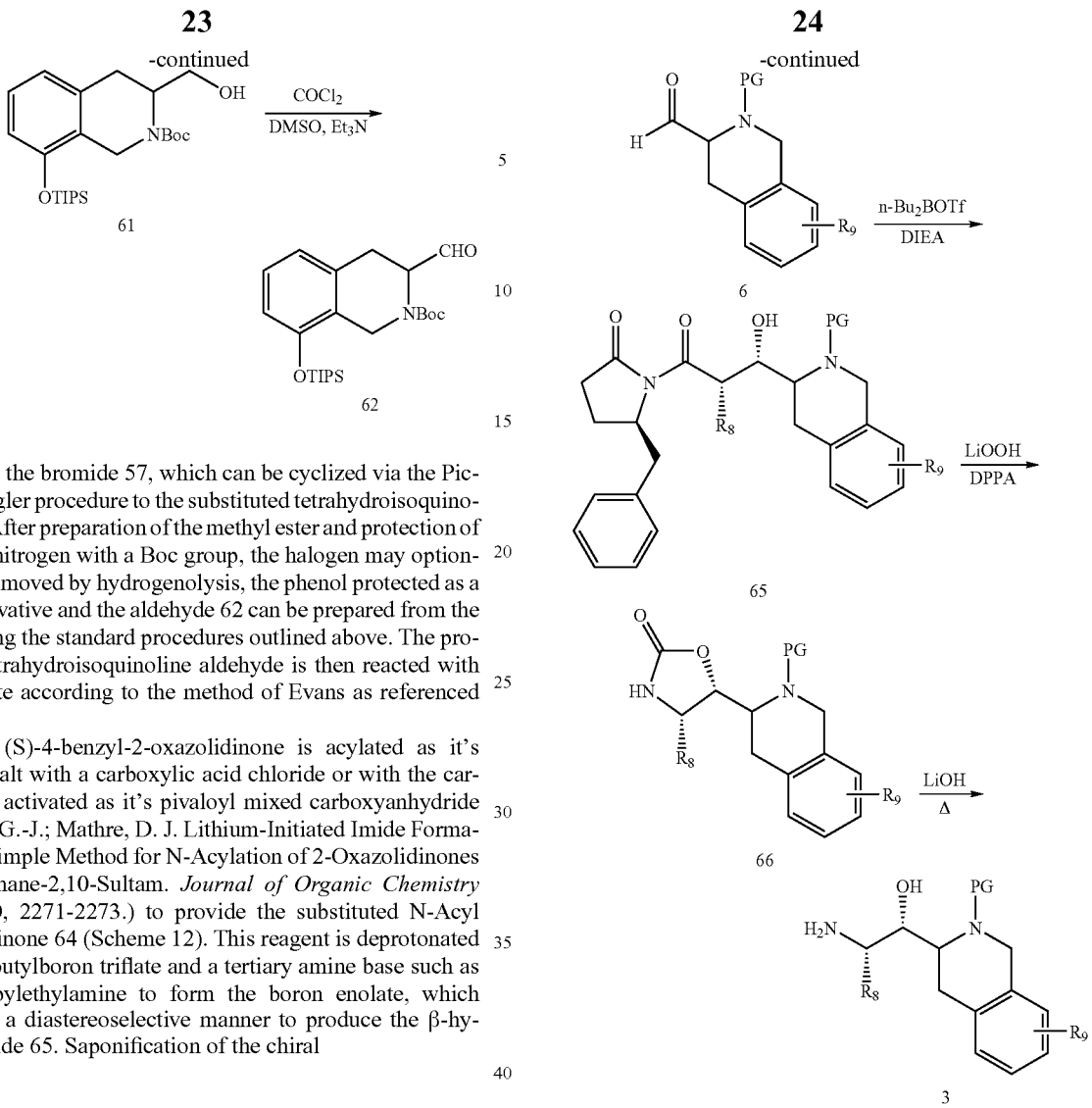

produces the bromide 57, which can be cyclized via the Pictet-Spengler procedure to the substituted tetrahydroisoquinoline 58. After preparation of the methyl ester and protection of the free nitrogen with a Boc group, the halogen may optionally be removed by hydrogenolysis, the phenol protected as a silyl derivative and the aldehyde 62 can be prepared from the ester using the standard procedures outlined above. The protected tetrahydroisoquinoline aldehyde is then reacted with an enolate according to the method of Evans as referenced above.

Thus, (S)-4-benzyl-2-oxazolidinone is acylated as it's lithium salt with a carboxylic acid chloride or with the carboxylate activated as it's pivaloyl mixed carboxyanhydride (see Ho, G.-J.; Mathre, D. J. Lithium-Initiated Imide Formation. A Simple Method for N-Acylation of 2-Oxazolidinones and Bornane-2,10-Sultam. *Journal of Organic Chemistry* 1995, 60, 2271-2273.) to provide the substituted N-Acyl oxazolidinone 64 (Scheme 12). This reagent is deprotonated using dibutylboron triflate and a tertiary amine base such as diisopropylethylamine to form the boron enolate, which reacts in a diastereoselective manner to produce the β-hydroxyimide 65. Saponification of the chiral Scheme 12

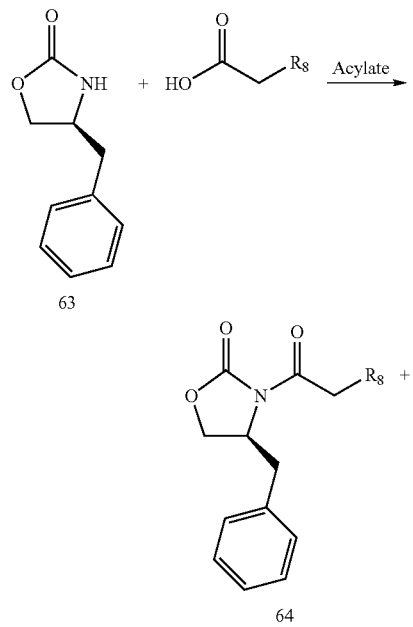

auxiliary under standard conditions (LiOH, $H_2O_2$) followed by Curtius rearrangement initiated by formation of the acyl azide using diphenylphosphorylazide (DPPA) provides the carbamate-protected aminoalcohol 66. Alternatively, the acid can be converted to the acyl azide using an acid activating agent such as the mixed carbonic anhydride formed by isobutyl chloroformate in the presence of an amine base such as N-methyl morpholine followed by treatment with sodium azide. The rearrangement is then cleanly effected by heating the acyl azide in a solvent such as toluene. At this point, easy manipulation of the tetrahydroisoquinoline nitrogen to other protecting groups is possible, preferred groups include p-methoxybenzyl which can be introduced in the usual way by reductive alkylation with p-anisaldehyde, or benzhydryl or suberyl which can be introduced using the corresponding halide. Cleavage of the carbamate by saponification with aqueous lithium hydroxide provides the functionalized tetrahydroisoquinoline-containing diaminopropane ready to couple to a substituted lactam 3.

Alternatively, intermediate 62 can be deprotected with tetrabutyl ammonium fluoride (TBAF) to provide the phenol, which can then be alkylated, or alternatively converted to the triflate and coupled with a palladium source to boronic acids to produce additional functionalized tetrahydroisoquinolines diaminopropanes 3a after LiOH deprotection (Scheme 13).

Scheme 13

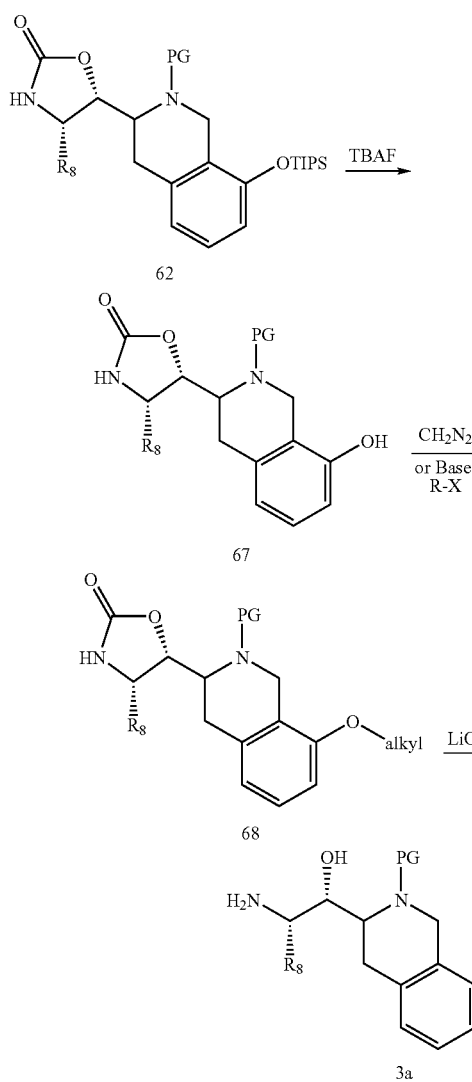

Coupling of a lactam acid 2 with a protected or unprotected amino alcohol 3 using methods previously described for making amide bonds, such as HATU and DIEA in DMF, provides a protected or unprotected product, which can be deprotected if necessary to provide the compounds Ia of the present invention (Scheme 14). Preferably, if a protecting group X is used, it is a Boc group, which is removed by treatment with trifluoroacetic acid in dichloromethane. Also preferred is cleavage of a p-methoxybenzyl or benzhydryl group using hydrogenation in the usual manner.

Scheme 14

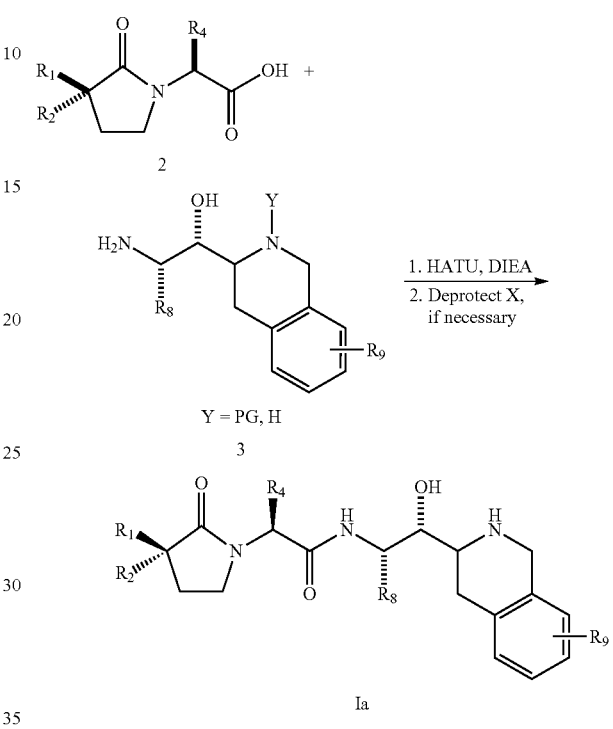

Intermediates of type 69 can be purchased commercially or prepared from commercial indole or azaindole gramine intermediates. Reaction with hexamethylenetetramine under protic conditions forms the aldehyde 70 (Scheme 15). Separately, Acyl imidazolides of amines (72) can be formed and reacted with methyl iodide to provide imidazoliniums 73 which react with the free (aza)indole nitrogen to provide the ureas 71. Oxidation of the aldehyde to the acid under standard conditions (for instance, using the Kraus oxidation) provides the (aza)indole acid 8 ready for coupling to a substituted amine 3.

Scheme 15

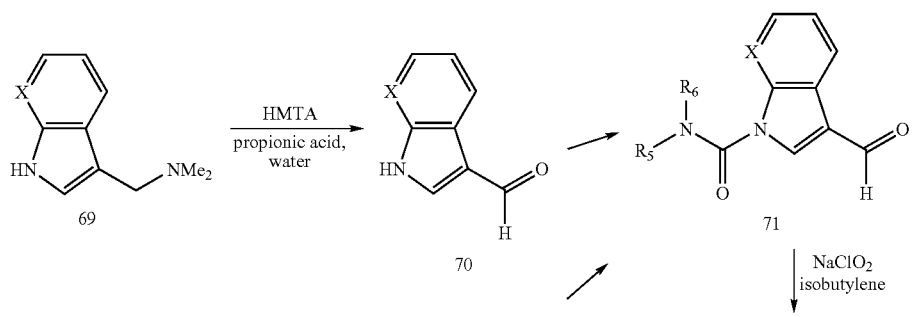

Coupling followed by deprotection if necessary of a protecting group provides the final compounds Ib (Scheme 16).

Scheme 16

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:
"Ac" for acetate,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDCl$_3$" for deuterochloroform,
"DCM" for dichloromethane
"DIEA", "Hunig's base", or "DIPEA" for N,N-diisopropylethylamine,
"DME" for 1,2-dimethoxyethane,
"DMF" for N,N-dimethylformamide,
"DMAP" for 4-dimethylaminopyridine,
"DMSO" for dimethylsulfoxide,
"EDC" or "EDCI" for 1-(3-dimethylaminopropyl)-3-ethyl-carbodiimide hydrochloride,
"Et" for ethyl,
"EtOAc" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMTA" for hexamethylenetetraamine
"LDA" for lithium diisopropylamide,
"LiHMDS" for lithium bis(trimethylsilyl)amide,
"n-BuLi" for n-butyllithium,
"NMM" for 4-methylmorpholine,
"PyBOP" for benzotriazole-1-yl-oxy-tris-pyrrolidino-phosphonium hexafluorophosphate,
"TBTU" for O-(1H-benzotriazol-1-yl)-N,N,N',N'-tetramethyluronium tetrafluoroborate,
"TEA" for triethylamine,
"TES" for triethylsilane,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min.

Reverse phase preparatory HPLC: When described as performed under "standard conditions", samples (approx. 20 mg) were dissolved in methanol (10 mg/mL) and purified on a 30 mm×100 mm Waters-Atlantis S5 column or a Phenomenex-Luna 30×100 mm 10 μm C18 column using a 10 minute gradient elution from 0% to 100% buffer B in buffer A (buffer A=10% MeOH/90% water/0.1% TFA and buffer B=90% MeOH/10% water/0.1% TFA). at 40 mL/minute.

Analytical HPLC: When described as "Method A", a sample dissolved in a suitable carrier solvent (methanol, acetonitrile, or the like) was analyzed on an Xterra 3.0×50 mm s7 column with a run time of 3 min and a gradient of 0-100% B over 2 min at a flowrate of 5 mL/min. Absorbance was monitored at 220 μM. Solvent A=0% MeOH/90% water/ 0.1% TFA and Solvent B=10% water/90% MeOH/0.1% TFA.

Analytical HPLC: When described as "Method B", a sample dissolved in a suitable carrier solvent (methanol, acetonitrile, or the like) was analyzed on an Xterra 3.0×50 mm s7 column with a run time of 4 min and a gradient of 0-100% B over 3 min at a flowrate of 5 mL/min. Absorbance was monitored at 220 μM. Solvent A=0% MeOH/90% water/ 0.1% TFA and Solvent B=10% water/90% MeOH/0.1% TFA.

Analytical HPLC: When described as "Method C", a sample dissolved in a suitable carrier solvent (methanol, acetonitrile, or the like) was analyzed on an Xterra 4.6×50 mm S5 column with a run time of 4 min and a gradient of 0-100% B over 2 min at a flowrate of 5 mL/min. Absorbance was monitored at 220 μM. Solvent A=0% MeOH/90% water/ 0.1% TFA and Solvent B=10% water/90% MeOH/0.1% TFA.

Analytical HPLC: When described as "Method D", a sample dissolved in a suitable carrier solvent (methanol, acetonitrile, or the like) was analyzed on an Phenomenex-LUNA 4.6×50 mm S10 column with a run time of 3 min and a gradient of 0-100% B over 2 min at a flowrate of 5 mL/min. Absorbance was monitored at 220 μM. Solvent A=10% MeOH/90% water/0.1% TFA and Solvent B=10% water/ 90% MeOH/0.1% TFA.

Proton NMR spectra (referenced to tetramethylsilane) were obtained on a Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

The examples provided are intended to assist in a further understanding of the present disclosure. Particular materials employed, species and conditions are intended to further illustrate the specific embodiments of the invention and not limit the reasonable scope thereof.

Synthesis of Intermediates

Preparation A (1S,2S)-1-((R)-2-(4-Methoxybenzyl)-1,2,3,4-tetrahydroisoquinolin-3-yl)-2-amino-3-(3,5-difluorophenyl) propan-1-ol

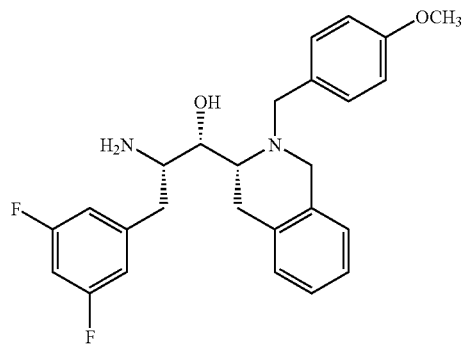

Step A (1): (R)-2-(tert-butoxycarbonyl)-1,2,3,4-tetrahydro-isoquinoline-3-carboxylic acid To a suspension of tetrahydroisoquinoline 3-carboxylic acid (H-D-Tic-OH) (purchased from Novabiochem) (4.1 g, 23.16 mmol) in 1,4-dioxane (100 mL) was added 1N aqueous sodium hydroxide solution (100 mL) and di-tert-butyldicarbonate (10.0 g, 46.33 mmol). The resulting reaction mixture was stirred at rt for 12 h. The mixture was then concentrated in vacuo to remove the solvent and 600 mL of ethyl acetate was added. 1N Aqueous hydrogen chloride solution was added to neutralize the reaction mixture to about pH 2. The organic phase was washed with 0.1 N aqueous NaCl, $H_2O$, and dried ($Na_2SO_4$), and concentrated in vacuo to give 6.3 g of the title compound (98% yield): $^1H$ NMR (CDCl$_3$, 500 MHz) δ 1.45 (9H, d, J=50 Hz), 3.14-3.25 (2H, m), 4.46 (1H, t, J=15 Hz), 4.67 (1H, t, J=15 Hz), 4.92 (1H, d, J=185 Hz), 7.07-7.17 (4H, m), 9.54 (1H, brd s)

Step A (2): (R)-tert-butyl 3-(hydroxymethyl)-3,4-dihydroisoquinoline-2(1H)-carboxylate To a solution of the compound of Step A (1) ((R)-2-(tert-butoxycarbonyl)-1,2,3,4-tetrahydroisoquinoline-3-carboxylic acid, 6.3 g, 23 mmol) in THF (200 mL) was added triethylamine (36.5 mmol) followed by ethyl chloroformate (27.3 mmol). The mixture was stirred at rt for 2 h. NaBH$_4$ (91.0 mmol) was then added and the mixture was stirred for 10 min. To the resulting mixture was added MeOH (40 ml) very slowly. When the addition was complete, the mixture was stirred for 3 h. The reaction was then concentrated in vacuo and the residue was partitioned between 1N NaOH and ethyl acetate (600 mL). The organic phase was washed with $H_2O$, dried ($Na_2SO_4$), and concentrated in vacuo to give 5.5 g (91%) of the title compound: $^1H$ NMR (CDCl$_3$, 500 MHz) δ 1.49 (9H, s), 3.02 (1H, dd, J=5, 15 Hz), 3.50 (2H, brd s), 3.61 (1H, d, J=10 Hz), 4.30 (1H, d, J=15 Hz), 4.44-4.52 (1H, m), 4.67-4.76 (1H, m), 7.09-7.18 (4H, m). MS (ESI) (M+H)$^+$ 264.19.

Step A (3): (R)-tert-butyl 3-formyl-3,4-dihydroisoquinoline-2(1H)-carboxylate To a solution of oxalyl dichloride (1.14 g, 9 mmol) in dichloromethane (30 mL) was added dimethyl sulfoxide (1.4 g, 18 mmol) at −78° C. After stirring at −78° C. for 20 min, to the mixture was added a solution of (R)-tert-butyl3-(hydroxymethyl)-3,4-dihydroisoquinoline-2(1H)-carboxylate (Step A (2), 1.32 g, 5 mmol) in dichloromethane (30 mL) and stirred at −78° C. for 30 to 45 min. Then triethylamine (36 mmol) was added and the reaction mixture was warmed up to rt over 2 h. Saturated sodium carbonate solution was added and extracted with dichloromethane. The solvent was removed and the crude mixture was purified by silica gel Flash chromatography to give the title compound: 1.2 g (90% yield). $^1$H NMR (CDCl$_3$, 500 MHz) δ 1.48 (9H, d, J=35 Hz), 3.06-3.62 (2H, m), 4.45-4.81 (3H, m), 7.09-7.19 (4H, m), 9.48 (1H, d, J=25 Hz).

Step A (4): (R)-tert-butyl 3-((1S,2S)-2-(3,5-difluorobenzyl)-3-((S)-4-benzyl-2-oxooxazolidin-3-yl)-1-hydroxy-3-oxopropyl)-3,4-dihydro-isoquinoline-2(1H)-carboxylate To a solution of (S)-4-benzyl-3-(3-(3,5-difluorophenyl)propanoyl)oxazolidin-2-one (preparation D, 1.3 g, 3.77 mmol) in CH$_2$Cl$_2$ (50 mL) at −78° C. was added Bu$_2$BOTf (4.90 ml, 4.90 mmol, 1M in CH$_2$Cl$_2$) and Hunig's base (972 mg, 7.54 mmol). The resulting mixture was brought up to 0° C. and stirred for 20 min. The mixture was cooled back to −78° C. and a solution of (R)-tert-butyl 3-formyl-3,4-dihydroisoquinoline-2(1H)-carboxylate (Step A (3), 1.10 g, 4.20 mmol) in CH$_2$Cl$_2$ (50 mL) was added dropwise. When the addition was complete, the mixture was allowed to warm to rt. After stirring at rt for 1 h, MeOH was added and the mixture was concentrated in vacuo. The crude mixture was purified by silica gel Flash chromatography to give 1.78 g (78% yield) of the title compound. MS (ESI)(M+H)$^+$ 607.20.

Step A (5): (2S,3S)-2-(3,5-difluorobenzyl)-3-((R)-2-(tert-butoxycarbonyl)-1,2,3,4-tetrahydroisoquinolin-3-yl)-3-hydroxypropanoic acid To a solution of (R)-tert-butyl 3-((1S,2S)-2-(3,5-difluorobenzyl)-3-((S)-4-benzyl-2-oxooxazolidin-3-yl)-1-hydroxy-3-oxopropyl)-3,4-dihydroisoquinoline-2(1H)-carboxylate (Step A (4), 13.0 g, 21.5 mmol) in THF (500 mL) was added a solution of LiOH (1.03 g, 43 mmol) in H$_2$O (100 mL), then 30% H$_2$O$_2$ (24.4 g) was added at 0° C. This reaction mixture was warmed up to rt over 1 h and stirred at rt for 4 h. Ethyl acetate (1000 mL) was added and washed with 1N HCl, and H$_2$O, dried (Na$_2$SO$_4$), and concentrated in vacuo to give the crude product which was ready for next step without purification. MS (ESI) (M−H)$^−$ 446.07.

Step A (6): (R)-tert-butyl 3-((4S,5S)-4-(3,5-difluorobenzyl)-2-oxooxazolidin-5-yl)-3,4-dihydroisoquinoline-2(1H)-carboxylate To a solution of (2S,3S)-2-(3,5-difluorobenzyl)-3-((R)-2-(tert-butoxycarbonyl)-1,2,3,4-tetrahydroisoquinolin-3-yl)-3-hydroxypropanoic acid (Step A (5), 2.9 mmol) in toluene (30 mL) was added diphenylphosphoryl azide (1.28 g, 4.64 mmol) and triethylamine (730 mg, 7.75 mmol.). This reaction mixture was brought to 40° C. for 2 h and 80° C. for 6 h. The mixture was partitioned between ethyl acetate (300 mL) and H$_2$O, dried over Na$_2$SO$_4$ and concentrated. The crude mixture was purified by silica gel Flash Chromatography to give 410 mg of the title compound (32% yield): $^1$H NMR (CDCl$_3$, 500 MHz) δ 1.53 (9H, m), 2.46-2.53 (1H, m), 2.90-3.00 (2H, m), 3.26 (1H, dd, J=5, 20 Hz), 3.78-3.81 (1H, m), 4.29-4.38 (1H, m), 4.43-4.50 (1H, m), 4.86-5.02 (2H, m), 5.13-5.18 (1H, m), 6.75 (3H, d, J=10 Hz), 7.13-7.24 (4H, m). MS (ESI)(M−H)$^−$ 443.05.

Step A (7): (4S,5R)-4-(3,5-difluorobenzyl)-5-((R)-1,2,3,4-tetrahydroisoquinolin-3-yl)oxazolidin-2-one A solution of (R)-tert-butyl 3-((4S,5S)-4-(3,5-difluorobenzyl)-2-oxooxazolidin-5-yl)-3,4-dihydroisoquinoline-2(1H)-carboxylate (Step A (6), 400 mg) in CH$_2$Cl$_2$ (20 mL) was treated with TFA (10 mL). This reaction mixture was stirred at rt for 3 h. The mixture was then concentrated in vacuo with addition of toluene. The residue was partitioned between ethyl acetate (200 mL) and aqueous sodium carbonate solution. The organic phase was washed again with aqueous sodium carbonate solution, H$_2$O, and dried (Na$_2$SO$_4$), and concentrated in vacuo to give 320 mg (100% yield) of the title compound: $^1$H NMR (CDCl$_3$, 500 MHz) δ 2.62 (1H, dd, J=10, 15 Hz), 2.66 (1H, dd, J=10, 15 Hz), 3.10 (1H, dd, J=5, 15 Hz), 3.24 (1H, dt, J=5, 10 Hz), 3.33 (1H, dd, J=5, Hz), 3.98 (2H, s), 4.05 (1H, m), 4.39 (1H, m), 5.64 (1H, s), 6.70 (1H, m), 6.76 (2H, d, J=10 Hz), 7.02 (1H, t, J=5 Hz), 7.12-7.17 (3H, m).

Step A (8): (4S,5S)-4-(3,5-difluorobenzyl)-5-((R)-2-(4-methoxybenzyl)-1,2,3,4-tetrahydroisoquinolin-3-yl)oxazolidin-2-one To a solution of (4S,5R)-4-(3,5-difluorobenzyl)-5-((R)-1,2,3,4-tetrahydroisoquinolin-3-yl)oxazolidin-2-one (Step A(7), 320 mg, 0.93 mmol) in THF (20 mL) was added 4-methoxybenzaldehyde (253 mg, 1.86 mmol) and acetic acid (2 drops). This mixture was stirred at rt overnight. NaBH(OAc)$_3$ (588 mg, 2.78 mmol) was added and the reaction mixture was stirred at rt for 2 days. Ethyl acetate (300 mL) was added and the mixture was washed with aqueous sodium carbonate, H$_2$O, dried (Na$_2$SO$_4$), and concentrated in vacuo. Crude mixture was purified by silica gel Flash Chromatography to give 420 mg of the title compound (80% yield): $^1$H NMR (CDCl$_3$, 500 MHz) δ 2.57 (1H, t, J=10 Hz), 2.96 (1H, dd, J=5, 20 Hz), 3.17 (1H, dd, J=5, 15 Hz), 3.44-3.50 (2H, m), 3.68 (2H, dd, J=10, 45 Hz), 3.80 (3H, s), 3.84-3.88 (3H, m), 4.66 (1H, dd, J=5, 10 Hz), 5.29 (1H, s), 6.71-6.74 (3H, m), 6.88 (2H, d, J=10 Hz), 6.98 (1H, d, J=5 Hz), 7.15-7.21 (5H, m). MS (ESI) (M+H)$^+$ 465.12.

Step A (9): (1S,2S)-1-((R)-2-(4-methoxybenzyl)-1,2,3,4-tetrahydroisoquinolin-3-yl)-2-amino-3-(3,5-difluorophenyl)propan-1-ol To a solution of (4S,5S)-4-(3,5-difluorobenzyl)-5-((R)-2-(4-methoxybenzyl)-1,2,3,4-tetrahydroisoquinolin-3-yl)oxazolidin-2-one (Step A (8), 420 mg, 0.9 mmol) in EtOH (20 mL) was added a solution of LiOH (217 mg, 9 mmol) in H$_2$O (5 mL). This reaction mixture was brought to 60° C. and stirred overnight. The mixture was then concentrated in vacuo. Ethyl ether (100 mL) was added to the mixture and washed with 1N HCl (80 mL) twice. The aqueous phase was basified to pH 12 with 50% aqueous NaOH solution. This mixture was extracted with ethyl acetate (100 mL) twice. The combined organic layer was dried (Na$_2$SO$_4$), and concentrated in vacuo to give 345 mg of the title compound of Preparation A: $^1$H NMR (CDCl$_3$, 500 MHz) δ 1.78 (2H, brd s), 2.44 (1H, dd, J=10, 15 Hz), 2.93 (1H, m), 3.01-3.07 (3H, m), 3.36 (1H, s), 3.60-3.69 (3H, m), 3.80 (3H, s), 6.69 (1H, m), 6.77-6.81 (2H, m), 6.86 (2H, d, J=10 Hz), 6.98 (1H, d, J=5 Hz), 7.12-7.18 (3H, m), 7.24 (2H, d, J=10 Hz). MS (ESI)(M+H)⁺ 439.12.

Preparation B (S)-2-((S)-3-Acetamido-3-((S)-sec-butyl)-2-oxopyrrolidin-1-yl)-4-phenylbutanoic acid

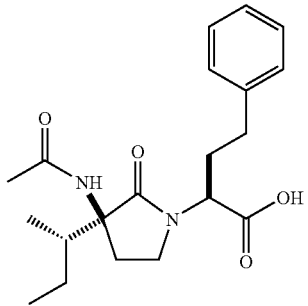

Step B (1): Sodium (2S,E)-2-(benzylideneamino)-3-methylpentanoate

L-Isoleucine (10.0 g, 76.24 mmol), benzaldehyde (8.57 g, 76.24 mmol) and 4 Å molecular sieves (20 g) were added to a solution of NaOH (3.05 g, 76.24 mmol) in anhydrous MeOH (100 mL). The mixture was stirred at rt for 16 h. After removal of the molecular sieves by filtration through celite, the filtrate was evaporated under reduced pressure to give a solid, which was further dried under vacuum for 8 h to give 18.0 g of the desired Schiff base (98%) as an off-white solid. ¹H NMR (DMSO-d₆) δ 8.12 (s, 1H), 7.65 (m, 2H), 7.36 (m, 3H), 2.45 (m, 1H), 1.38 (m, 1H), 0.91 (m, 1H), 0.76 (m, 6H).

Step B (2): (2S,4S)-benzyl 4-sec-butyl-5-oxo-2-phenyloxazolidine-3-carboxylate

To 250 mL of CH₂Cl₂ was added the Schiff base from step B(1) (12.0 g, 49.74 mmol). The solution was cooled to −20° C., after which 10.7 mL (74.61 mmol, 1.5 eq) of benzyl chloroformate was added. The reaction solution was stirred at −20° C. for 96 h, warmed to room temperature, and diluted with CH₂Cl₂. The reaction mixture was washed 2× each with water, aq. NaHCO₃, aq. sodium bisulfite and water again. The organic layer was dried over MgSO₄, filtered, and the filtrate was concentrated and the residue was purified by chromatography on silica gel to give the desired product (11 g, 63%) as oil. APCI (M+H)⁺=354.3. ¹H NMR (CDCl₃) δ 7.54-7.26 (m, 10H), 6.76 (s, 1H), 5.23 (s, 2H), 4.36-4.34 (dd, J=5.8 Hz, 1H), 1.80 (m, 1H), 1.60-1.20 (m, 2H), 0.86-0.80 (m, 6H).

Step B (3): (2S,4S)-benzyl 4-allyl-4-sec-butyl-5-oxo-2-phenyloxazolidine-3-carboxylate The compound of Step B (2) (570 mg, 1.613 mmol) in 10 mL anhydrous of THF was cooled to −78° C. Then 0.22 mL (2.42 mmol, 1.5 eq) of allyl iodide was added followed by 4.8 mL of 0.5 N (2.4 mmol, 1.5 eq) potassium bis(trimethylsilyl) amide. TLC at 60 min showed the reaction was complete, so it was quenched with aqueous NH₄Cl and warmed to room temperature. Then the solution was diluted with water and extracted with ethyl acetate. The combined ethyl acetate extracts were washed with dilute aqueous NH₄Cl, dried over MgSO₄, filtered, and the filtrate was concentrated. The residue was purified by silica gel chromatography to give 567 mg (89%) of the title compound. ESI (M+H)⁺=394.4. ¹H NMR (CDCl₃) δ 7.42-7.26 (m, 10H), 6.34 (s, 1H), 5.68-5.57 (m, 1H), 5.16-5.12 (dd, J=9 Hz, 2H), 5.06 (s, 2H), 2.72-2.66 (m, 2H), 1.70-1.30 (m, 2H), 1.12-0.88 (m, 6H).

Step B (4): (S)-2-(benzyloxycarbonyl)-2-((S)-sec-butyl)pent-4-enoic acid

The compound from step B (3) (567 mg, 1.44 mmol) of was dissolved in 40 mL of THF-MeOH (3:1). 10 mL 2N NaOH was added and the mixture was refluxed for 2 h. The THF and MeOH was evaporated, diluted ethyl acetate and acidified with HCl. Extracted 2× with ethyl acetate, dried the organic layer with MgSO₄, filtered and the filtrate was evaporated. The residue was pumped on high vacuum to give crude acid 695 mg. ESI (M−H)⁻=304.3.

Step B (5): (S)-ethyl 2-((S)-2-(benzyloxycarbonyl)-2-((S)-sec-butyl)pent-4-enamido)-4-phenylbutanoate The acid (695 mg, 2.27 mmol) from step B (4), 15 mL of CH₂Cl₂, 488 mg HOBt (3.19 mmol, 1.4 eq) and 655 mg EDC (3.42 mmol, 1.5 eq) were mixed and stirred for 5 min. 660 mg (3.42 mmol, 1.5 eq) of homo-Phe methyl ester and 0.80 mL of DIEA (5.68 mmol, 2.5 eq) were then added and the mixture was stirred for 4 h. The reaction solution was diluted with ethyl acetate and washed with 5% citric acid and 5% NaHCO₃, dried over MgSO₄, filtered, and the filtrate was evaporated. The residue was purified by silica gel chromatography to provide Amide 0.53 g (76.7% for steps 2d and 2e). ESI (M+H)⁺=481.5. ¹H NMR (CDCl₃) δ 7.36-7.14 (m, 10H), 5.80-5.65 (m, 2H), 5.20-5.00 (m, 2H), 5.08 (s, 2H), 4.65-4.55 (m, 1H), 3.70 (s, 3H), 2.90-1.90 (m, 7H), 1.63-1.00 (m, 2H), 1.00-0.91 (m, 6H).

Step B (6): (S)-ethyl 2-((3S)-3-(benzyloxycarbonyl)-3-((R)-sec-butyl)-5-hydroxy-2-oxopyrrolidin-1-yl)-4-phenylbutanoate Ozone was bubbled through a solution of alkene from step B(5) in 10 mL of CH₂Cl₂ (0.78 g, 1.62 mmol) at −78° C. until a blue color persisted. Residual ozone was removed with a stream of oxygen. Triphenyl phosphine (0.60 g, 2.29 mmol) was added, and the reaction mixture was allowed to warm to rt. After 1 h, the solution was concentrated under reduced pressure. The residue was purified by chromatography on silica gel to provide aldehyde 0.47 g (61%). ESI (M+H)⁺=483.4, (M+Na)⁺=505.4.

Step B (7): (S)-ethyl 2-((S)-3-(benzyloxycarbonyl)-3-((R)-sec-butyl)-2-oxopyrrolidin-1-yl)-4-phenylbutanoate A solution of TFA/Et₃SiH (1:1, 5 mL) was added to the solution of aldehyde from step B (6) (0.47 g, 0.97 mmol) in 10 mL of CH₂Cl₂ at 0° C. The mixture was stirred at 0° C. for 3 h. The reaction solution was concentrated under reduced pressure. The residue was purified by chromatography on silica gel to provide lactam 0.23 g (50%). ESI (M+H)⁺=467.38. ¹H NMR (CDCl₃) δ 7.34-7.16 (m, 10H), 5.45 (br, 1H), 5.05 (s, 2H), 4.87-4.82 (dd, J=4 Hz, 1H)), 3.65-3.35 (m, 2H), 3.67 (s, 3H), 2.90-1.45 (m, 8H), 1.20-1.00 (m, 1H), 0.98-0.90 (m, 6H).

Step B (8): (S)-ethyl 2-((S)-3-amino-3-((R)-sec-butyl)-2-oxopyrrolidin-1-yl)-4-phenylbutanoate A solution of lactam from step B(7) (225 mg, 0.48 mmol) in methanol (15 mL) was hydrogenated over 10% palladium on carbon (40 mg) for 16 h. The solution was filtered through celite and concentrated under reduced pressure to afford the desired amine. ESI (M+H)$^+$=333.4. $^1$H NMR (CDCl$_3$) δ 7.29-7.16 (m, 5H), 4.78-4.60 (m, 3H), 3.68 (s, 3H), 3.44-3.37 (m, 2H), 2.68-1.85 (m, 8H), 1.20-1.00 (m, 1H), 0.96-0.91 (m, 6H).

Step B (9): (S)-ethyl 2-((S)-3-acetamido-3-((R)-sec-butyl)-2-oxopyrrolidin-1-yl)-4-phenylbutanoate A mixture of acetic acid (54 µL, 0.91 mmol), HATU (348 mg, 0.92 mmol), and DIEA (257 µL, 0.91 mmol) in 5 mL of DMF was stirred at room temperature for 5 min. Amine (152 mg, 0.46 mmol) from step B(8) in 1 mL of DMF was added and the solution was continued to stir for overnight. The reaction solution was diluted with ethyl acetate and washed 3× with water, 1× brine, dried the organic layer with MgSO$_4$, filtered and the filtrate was evaporated. The residue was purified by chromatography on silica gel to provide lactam 160 mg (94%). ESI (M+H)$^+$=375.2. $^1$H NMR (CDCl$_3$) δ 7.33-7.17 (m, 5H), 6.07 (br, 1H), 4.66-4.61 (m, 1H), 3.73 (s, 3H), 3.60-3.20 (m, 2H), 2.70-1.60 (m, 8H), 1.20-1.00 (m, 1H), 0.98-0.86 (m, 6H).

Step B (10): (S)-2-((S)-3-acetamido-3-sec-butyl-2-oxopyrrolidin-1-yl)-4-phenylbutanoic acid The compound from step B(9) (0.20 g, 0.53 mmol) was dissolved in 5 mL of THF/H$_2$O (4:1). LiOH (120 mg, 2.9 mmol) was added and the mixture was stirred for 16 h. It was then diluted with ethyl acetate and acidified with 1 N HCl. The aqueous layer was extracted with 3× ethyl acetate. The combined organic layer was dried over MgSO$_4$, filtered and evaporated under reduced pressure to give the acid of preparation B (98 mg, 85%). ESI (M−H)$^−$=359.2.

Preparation C (S)-2-((R)-3-Acetamido-3-isobutyl-2-oxopyrrolidin-1-yl)-4-phenylbutanoic acid

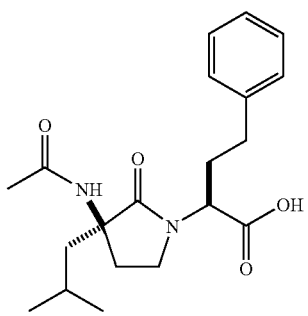

In a manner similar to the synthesis of the compound of preparation B, L-Leucine was converted to the compound of preparation C. $^1$H NMR (400 MHz, CDCl$_3$) δ ppm 0.92 (dd, J=16.26, 6.24 Hz, 6H) 1.62 (m, 1H) 1.81 (m, 2H) 1.98 (s, 3H) 2.11 (m, 1H) 2.31 (m, 3H) 2.44 (m, J=2.69 Hz, 1H) 2.68 (m, 2H) 3.39 (m, 2H) 4.72 (dd, J=10.88, 4.52 Hz, 1H) 6.11 (s, 1H) 7.19 (m, 3H) 7.27 (m, 2H).

Preparation D (S)-4-Benzyl-3-(3-(3,5-difluorophenyl)propanoyl)oxazolidin-2-one

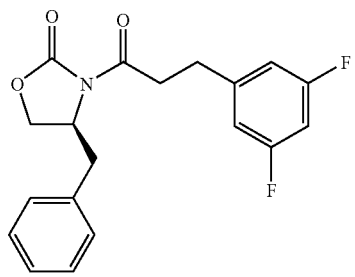

Step D (1): (3-(3,5-difluorophenyl)propanoic acid

To palladium on activated charcoal (10 wt %, 2.5 g) was added a solution of (E)-3-(3,5-difluorophenyl)acrylic acid (25 g) in a mixture of ethyl acetate (100 mL) and ethyl alcohol (400 mL). The mixture was put on hydrogenator on 50 psi for 6 h. The catalyst was filtered and the solvent was removed to give 25.0 g the title compound (99% yield): $^1$H NMR (CDCl$_3$, 500 MHz) δ 2.67 (2H, t, J=10 Hz), 2.93 (2H, t, J=10 Hz), 6.65 (1H, m), 6.72 (2H, m).

Step D (2): (S)-4-benzyl-3-(3-(3,5-difluorophenyl)propanoyl)-oxazolidin-2-one To a solution of (3-(3,5-difluorophenyl)propanoic acid (Step D (1), 2.0 g, 10.75 mmol) in dichloromethane (50 mL) was added oxalyl dichloride (1.92 g, 15.05 mmol). DMF (0.5 mL) was added dropwise at rt to generate lots of bubbles. The mixture was stirred at rt for 2 h and the solvent was removed to give a crude residue. To a solution of (S)-4-benzyloxazolidin-2-one (2.1 g, 11.8 mmol) in THF (40 mL) was added n-BuLi (2.0 M solution in hexanes, 6.45 mL) at −78° C. After stirring for 30 min., the mixture was warmed up to 0° C. and then cooled back to −78° C. Then a solution of the above residue in THF (60 mL) was added at −78° C. The reaction mixture was allowed to warm to rt over 2 h. The solvents were removed and the crude mixture was purified by silica gel chromatography to give 3.2 g of the title compound of preparation D (86% yield). $^1$H NMR (CDCl$_3$, 500 MHz) δ 2.74-2.79 (1H, m), 2.98-3.01 (2H, m), 3.18-3.33 (3H, m), 4.15-

4.22 (2H, m), 4.65-4.69 (1H, m), 6.64 (1H, m), 6.79 (2H, d, J=10 Hz), 7.16 (2H, d, J=5 Hz), 7.25-7.28 (1H, m), 7.30-7.33 (2H, m).

Preparation E (1S,2S)-2-Amino-3-(3,5-difluorophenyl)-1-((S)-2-(5-dibenzosuberyl)-1,2,3,4-tetrahydroisoquinolin-3-yl)propan-1-ol

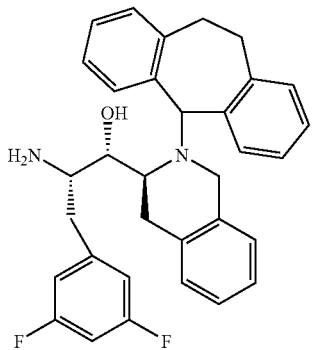

Step E (1): (S)-tert-butyl 3-((4S,5S)-4-(3,5-difluorobenzyl)-2-oxooxazolidin-5-yl)-3,4-dihydroisoquinoline-2(1H)-carboxylate In a manner similar to the preparation of the compound of step A (6), but beginning the synthesis sequence with racemic tetrahydroquinoline carboxylic acid, a mixture of the compounds of Step E (1) and the compound of step A (6) were prepared. The 2 isomers can be separated on silica gel and isolated in pure form. $^1$H NMR (CDCl$_3$, 500 MHz) δ 1.53 (9H, m), 2.51 (1H, t, J=15 Hz), 2.90-3.01 (2H, m), 3.26 (1H, d, J=15 Hz), 3.80 (1H, m), 4.30-4.38 (1H, m), 4.47-4.51 (1H, m), 4.86-4.92 (2H, m), 6.75 (3H, d, J=10 Hz), 7.13-7.24 (4H, m).

Step E (2): (4S,5R)-4-(3,5-difluorobenzyl)-5-((S)-1,2,3,4-tetrahydroisoquinolin-3-yl)oxazolidin-2-one A solution of (S)-tert-butyl 3-((4S,5S)-4-(3,5-difluorobenzyl)-2-oxooxazolidin-5-yl)-3,4-dihydroisoquinoline-2(1H)-carboxylate (step E (1), 550 mg) in CH$_2$Cl$_2$ (20 mL) was treated with TFA (10 mL). This reaction mixture was stirred at rt for 2 h. The mixture was then concentrated in vacuo with addition of toluene. The residue was added 1N aqueous HCl solution (50 mL) and washed with diethyl ether (80 mL). The diethyl ether layer was washed with 1N aqueous HCl solution again. The combined aqueous layers were neutralized with 50% aqueous NaOH solution, extracted with ethyl acetate. The organic phase was washed with H$_2$O, and dried (Na$_2$SO$_4$), and concentrated in vacuo to give 350 mg (81% yield) of the title compound: $^1$H NMR (CDCl$_3$, 500 MHz) δ 2.23 (1H, brd s), 2.72 (1H, dd, J=5, 15 Hz), 2.88 (1H, dd, J=10, 15 Hz), 3.02 (1H, m), 3.10 (1H, dd, J=10, 15 Hz), 3.22 (1H, m), 4.06 (2H, s), 4.12 (1H, m), 4.63 (1H, m), 5.64 (1H, s), 6.69-6.77 (3H, m), 7.04 (1H, t, J=5 Hz), 7.08 (1H, t, J=5 Hz), 7.12-7.15 (2H, m).

Step E (3): (4S,5R)-4-(3,5-difluorobenzyl)-5-(2-(5-dibenzosuberyl)-(S)-1,2,3,4-tetrahydroisoquinolin-3-yl)oxazolidin-2-one To a solution of (4S,5R)-4-(3,5-difluorobenzyl)-5-((S)-1,2,3,4-tetrahydroisoquinolin-3-yl)oxazolidin-2-one (Step E (2), 100 mg, 0.29 mmol) in THF (1 mL) and diethyl ether (3 mL) was added dibenzosuberyl chloride (100 mg, 0.435 mmol) and silver nitrate (0.435 mmol). This mixture was stirred at rt for 5 h. Then another batch of dibenzosuberyl chloride (100 mg, 0.435 mmol) and silver nitrate (0.435 mmol) were added and the reaction mixture was stirred at rt overnight. Ethyl acetate (100 mL) was added and the mixture was washed with aqueous sodium carbonate, H$_2$O, dried, and concentrated in vacuo. Crude mixture was purified by silica gel Flash Chromatography to give 70 mg of the title compound (45% yield): $^1$H NMR (CDCl$_3$, 500 MHz) δ 2.07-2.13 (2H, m), 2.46 (1H, m), 2.74-2.87 (1H, m), 3.11 (1H, m), 3.56-3.65 (2H, m), 3.74 (1H, d, J=15 Hz), 3.84-3.98 (3H, m), 4.74 (1H, dd, J=5, 10 Hz), 5.24 (1H, s), 5.29 (1H, s), 6.50 (2H, d, J=5 Hz), 6.72 (1H, m), 6.95 (1H, t, J=5 Hz), 7.03 (1H, t, J=5 Hz), 7.07-7.14 (4H, m), 7.17-7.25 (4H, m), 7.37 (1H, d, J=10 Hz), 7.48 (1H, brd s). MS (ESI) (M−H)$^-$ 535.17.

Step E (4): (1S,2S)-2-amino-3-(3,5-difluorophenyl)-1-((S)-2-(5-dibenzosuberyl)-1,2,3,4-tetrahydroisoquinolin-3-yl)propan-1-ol To a solution of (4S,5R)-4-(3,5-difluorobenzyl)-5-(2-(5-dibenzosuberyl)-(S)-1,2,3,4-tetrahydroisoquinolin-3-yl)oxazolidin-2-one (Step E (3), 70 mg, 0.13 mmol) in EtOH (4 mL) was added a solution of LiOH (0.65 mmol) in H$_2$O (1 mL). This reaction mixture was brought to 95° C. and stirred overnight. Ethyl ether (100 mL) was added to the mixture and washed with sodium carbonate solution, dried (Na$_2$SO$_4$), and concentrated in vacuo to give 60 mg of the title compound of preparation E. $^1$H NMR (CDCl$_3$, 500 MHz) δ 2.28 (1H, dd, J=10, 15 Hz), 2.44 (1H, d, J=10 Hz), 2.50 (1H, d, J=15 Hz), 2.72 (1H, brd s), 2.90-3.02 (2H, m), 3.09-3.17 (2H, m), 3.53-3.62 (2H, m), 3.80 (1H, m), 3.88 (1H, d, J=15 Hz), 3.92-3.98 (1H, m), 4.53 (1H, s), 6.58 (1H, d, J=5 Hz), 6.63 (1H, m), 6.80 (2H, m), 7.01-7.24 (10H, m).

Preparation F (1S,2S)-1-((R)-8-(allyloxy)-2-Benzhydryl-1,2,3,4-tetrahydroisoquinolin-3-yl)-2-amino-3-(3,5-difluorophenyl)propan-1-ol

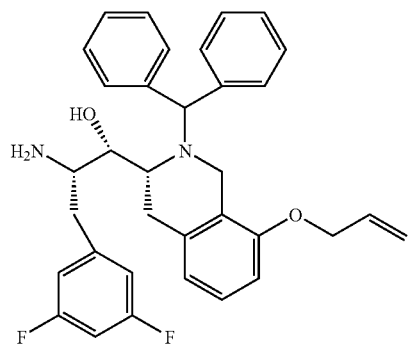

Step F (1): 2-amino-3-(2-bromo-5-hydroxyphenyl propanoic acid

To a solution of 2-amino-3-(3-hydroxyphenyl)propanoic acid (Commercial, 15 g, 82.9 mmol) in acetic acid (700 mL) was added bromine (13.26 g, 82.9 mmol) in acetic acid (700 mL) slowly over 45 minutes at rt. The resulting reaction mixture was stirred at rt overnight. The precipitate was filtered to give the title compound (15.1 g, 70% yield): $^1$H NMR (CD$_3$OD, 500 MHz) δ 3.11 (1H, dd, J=5, 15 Hz), 3.42 (1H, m), 4.26 (1H, dd, J=5, 10 Hz), 6.70 (1H, dd, J=5, 10 Hz), 6.82 (1H, d, J=5 Hz), 7.41 (1H, d, J=10 Hz).

Step F (2): 5-bromo-8-hydroxy-1,2,3,4-tetrahydroisoquinoline-3-carboxylic acid

To a solution of 2-amino-3-(2-bromo-5-hydroxyphenyl) propanoic acid (Step F (1), 15.5 g, 45.6 mmol) in H$_2$O (500 mL) were added paraformaldehyde (37 wt % in H$_2$O, 15 eq.) and concentrated HCl (8 mL). The resulting reaction mixture was stirred at rt for 1.5 h and stirred at 60° C. for 1.5 h. Another batch of concentrated HCl (40 mL) was added and stirred for 30 min. Then the reaction mixture was stirred at 90° C. for 40 min. Solvent was removed to give the title compound: MS (ESI) (M+H)$^+$ 272.01.

Step F (3): Methyl 5-bromo-8-hydroxy-1,2,3,4-tetrahydro-isoquinoline-3-carboxylate hydrochloride To a solution of 5-bromo-8-hydroxy-1,2,3,4-tetrahydroisoquinoline-3-carboxylic acid (Step F (2), 45.6 mmol) in methanol (150 mL) was added thionyl chloride (25 mL) at 0° C. slowly under N$_2$. The resulting reaction mixture was stirred at rt overnight. Solvent was removed with addition of toluene (50 mL, 3 times) to give the title compound as a crude mixture: $^1$H NMR (CD$_3$OD, 500 MHz) δ 3.02 (1H, m), 3.44 (1H, dd, J=5, 15 Hz), 3.93 (3H, s), 4.19 (1H, d, J=20 Hz), 4.46-4.50 (2H, m), 6.72 (1H, d, J=5 Hz), 7.41 (1H, d, J=10 Hz). MS (ESI) (M+H)$^+$ 286.02.

Step F (4): 2-tert-butyl 3-methyl 5-bromo-8-hydroxy-3,4-dihydro-isoquinoline-2,3(1H)-dicarboxylate To a solution of methyl 5-bromo-8-hydroxy-1,2,3,4-tetrahydroisoquinoline-3-carboxylate (Step F (3), 45.6 mmol) in dichloromethane (200 mL) was added Hunig base (16 mL) and di-tert-butyldicarbonate (12.9 g, 60 mmol). The resulting reaction mixture was stirred at rt for 3 h. The mixture was then concentrated in vacuo to remove the solvent and 600 mL of ethyl acetate was added. The mixture was washed with 1 N aqueous HCl, H$_2$O, and dried (Na$_2$SO$_4$), and concentrated in vacuo to give the title compound (8.5 g) as a crude mixture. MS (ESI)(M+H)$^+$ 386.09.

Step F (5): 2-tert-butyl 3-methyl 8-hydroxy-3,4-dihydroisoquinoline-2,3(1H)-dicarboxylate To palladium on activated charcoal (1.0 g) was added a mixture of 2-tert-butyl 3-methyl 5-bromo-8-hydroxy-3,4-dihydroisoquinoline-2,3(1H)-dicarboxylate (Step F (4), 45.6 mmol) and Hunig's base (5 mL) in methanol (150 mL). The mixture was put on hydrogenator at 50 psi overnight. The resulting reaction mixture was filtered and concentrated in vacuo. The crude mixture was purified by silica gel Flash Chromatography to give the title compound (5.2 g): MS (ESI) (M−H)$^-$ 306.09.

Step F (6): 2-tert-butyl 3-methyl 8-(triisopropylsilyloxy)-3,4-dihydroisoquinoline-2,3(1H)-dicarboxylate To a solution of 2-tert-butyl 3-methyl 8-hydroxy-3,4-dihydroisoquinoline-2,3(1H)-dicarboxylate (Step F (5), 1.72 g, 5.6 mmol) in dichloromethane (100 mL) was added Hunig's base (2.17 g, 16.8 mmol), followed by TIPS-Cl (1.4 g, 7.28 mmol). The reaction mixture was stirred at rt overnight. Solvent was removed and the crude mixture was purified by silica gel Flash Chromatography to give the title compound (2.2 g, 85% yield): $^1$H NMR (CDCl$_3$, 500 MHz) δ 1.11 (18H, d, J=10 Hz), 1.18-1.33 (3H, m), 1.51 (9H, s), 3.08-3.26 (2H, m), 3.59 (3H, s), 4.40 (1H, d, J=20 Hz), 4.69 (1H, d, J=20 Hz), 5.16 (1H, m), 6.65 (1H, d, J=10 Hz), 6.71 (1H, d, J=10 Hz), 6.99-7.02 (1H, m).

Step F (7): tert-butyl 3-(hydroxymethyl)-8-(triisopropylsilyloxy)-3,4-dihydroisoquinoline-2(1H)-carboxylate To a solution of 2-tert-butyl 3-methyl 8-(triisopropylsilyloxy)-3,4-dihydroisoquinoline-2,3(1H)-dicarboxylate (Step F (6), 3.50 g, 7.56 mmol) in THF (100 mL) was added lithium aluminum hydride (1.0 M solution in THF, 6.0 mmol) at −10° C. The reaction mixture was stirred from −10° C. to −2° C. for 20 min. H$_2$O, 0.1 N aqueous HCl and 500 mL of ethyl acetate were added and the mixture was washed with H$_2$O, dried over Na$_2$SO$_4$, and concentrated in vacuo to give 3.40 g of the title compound: $^1$H NMR (CDCl$_3$, 500 MHz) δ 1.11 (18H, d, J=10 Hz), 1.22-1.33 (3H, m), 1.49 (9H, s), 2.74 (1H, m), 3.01 (1H, dd, J=5, 15 Hz), 3.51 (2H, s), 4.30-4.33 (1H, m), 4.60-4.70 (2H, m), 6.66 (1H, d, J=5 Hz), 6.70 (1H, d, J=5 Hz), 7.02 (1H, m).

Step F (8): tert-butyl 3-formyl-8-(triisopropylsilyloxy)-3,4-dihydroisoquinoline-2(1H)-carboxylate To a solution of oxalyl dichloride (787 mg, 6.2 mmol) in dichloromethane (40 mL) was added dimethyl sulfoxide (967 mg, 12.4 mmol) at −78° C. After stirring at −78° C. for 20 min, the mixture was added a solution of tert-butyl 3-(hydroxymethyl)-8-(triisopropylsilyloxy)-3,4-dihydroisoquinoline-2 (1H)-carboxylate (Step F (7), 1.5 g, 3.45 mmol) in dichloromethane (40 mL) and stirred at −78° C. for 30 to 45 min. Then Hunig base (2.67 g, 20.7 mmol) was added and the reaction mixture was warmed up to rt over 2 h. Saturated sodium carbonate solution was added and extracted with dichloromethane. The solvent was removed and the crude mixture was purified by silica gel Flash chromatography to give the title compound 1.2 g (80% yield): $^1$H NMR (CDCl$_3$, 500 MHz) δ 1.04-1.11 (18H, m), 1.23-1.33 (3H, m), 1.46-1.52 (9H, m), 3.03-3.24 (2H, m), 4.47-4.88 (3H, m), 6.65-6.68 (1H, m), 6.74 (1H, d, J=10 Hz), 7.02 (1H, m), 9.52 (1H, s).

Step F (9): tert-butyl 3-((1S,2S)-2-(3,5-difluorobenzyl)-3-((S)-4-benzyl-2-oxooxazolidin-3-yl)-β-hydroxy-3-oxopropyl)-8-(triisopropylsilyloxy)-3,4-dihydroisoquinoline-2(1H)-carboxylate To a solution of (s)-4-benzyl-3-(3-(3,5-difluorophenyl) propanoyl)-oxazolidin-2-one (1.05 g, 3.05 mmol) in CH$_2$Cl$_2$ (40 mL) at −78° C. was added Bu$_2$BoTf (3.6 ml, 3.6 mmol, 1M in CH$_2$Cl$_2$) and Hunig's base (893 mg, 6.9 mmol). The resulting mixture was brought up to 0° C. and stirred for 20 min. The mixture was cooled back to −78° C. and a solution of tert-butyl 3-formyl-8-(triisopropylsilyloxy)-3,4-dihydroisoquinoline-2(1H)-carboxylate (Step F (8), 1.2 g, 2.77 mmol) in CH$_2$Cl$_2$ (40 mL) was added dropwise. When the addition was complete, the mixture was allowed to warm to rt. After stirring at rt for 1 h, MeOH was added and the mixture was concentrated in vacuo. The crude mixture was purified by silica gel Flash chromatography to give 2.0 g (92% yield) of the title compound. MS (ESI) (M+H)⁺ 779.33.

Step F (10): (2S,3S)-2-(3,5-difluorobenzyl)-3-(2-(tert-butoxycarbonyl)-8-(triisopropylsilyloxy)-1,2,3,4-tetrahydroisoquinolin-3-yl)-3-hydroxypropanoic acid To a solution of tert-butyl 3-((1S,2S)-2-(3,5-difluorobenzyl)-3-((S)-4-benzyl-2-oxooxazolidin-3-yl)-1-hydroxy-3-oxopropyl)-8-(triisopropylsilyloxy)-3,4-dihydroisoquinoline-2(1H)-carboxylate (Step F (9), 2.0 g, 2.57 mmol) in THF (50 mL) was added a solution of LiOH (123 mg, 5.13 mmol) in $H_2O$ (8 mL), then 30% $H_2O_2$ (3.0 g, 25.7 mmol) was added at −5° C. This reaction mixture was stirred from −5° C. to 0° C. over 1 h and stirred at rt for 3 h. Solvent was removed and ethyl acetate (500 mL) was added. The mixture was washed with 1N HCl, and $H_2O$, dried ($Na_2SO_4$), and concentrated in vacuo to give the crude product which was ready for next step without purification. MS (ESI) (M−H)⁻ 618.22.

Step F (11): (R)-tert-butyl 3-((4S,5S)-4-(3,5-difluorobenzyl)-2-oxooxazolidin-5-yl)-8-(triisopropylsilyloxy)-3,4-dihydroisoquinoline-2(1H)-carboxylate To a solution of (2S,3S)-2-(3,5-difluorobenzyl)-3-(2-(tert-butoxycarbonyl)-8-(triisopropylsilyloxy)-1,2,3,4-tetrahydroisoquinolin-3-yl)-3-hydroxypropanoic acid (Step F (10), 2.0 g, 2.57 mmol) in toluene (150 mL) was added diphenylphosphoryl azide (1.13 g, 4.12 mmol) and triethyl amine (649 mg, 6.43 mmol.). This reaction mixture was brought to 50° C. for 2 h and 100° C. for 3 h. The mixture was concentrated under vacuum and purified by silica gel Flash Chromatography to give 470 mg of the title compound: ¹H NMR (CDCl₃, 500 MHz) δ 1.12 (18H, m), 1.28-1.36 (3H, m), 1.48 (9H, s), 2.71 (1H, m), 3.08 (2H, s), 3.18-3.22 (1H, m), 3.82 (1H, m), 4.59 (1H, m), 4.76-5.04 (2H, m), 5.11 (1H, s), 6.67-6.77 (5H, m), 7.06 (1H, m).

Step F(12): (4S,5R)-4-(3,5-difluorobenzyl)-5-((R)-8-(triisopropylsilyloxy)-1,2,3,4-tetrahydroisoquinolin-3-yl)oxazolidin-2-one A solution of (R)-tert-butyl 3-((4S,5S)-4-(3,5-difluorobenzyl)-2-oxooxazolidin-5-yl)-8-(triisopropylsilyloxy)-3,4-dihydroisoquinoline-2(1H)-carboxylate (Step F (11), 470 mg) in $CH_2Cl_2$ (20 mL) was treated with TFA (5 mL). This reaction mixture was stirred at rt for 3 h. The reaction mixture was then concentrated in vacuo. Ethyl acetate (10 mL) was added and removed and toluene (10 mL) was added and removed twice to give the title compound: ¹H NMR (CDCl₃, 500 MHz) δ 1.10 (18H, m), 1.30 (3H, m), 2.61-2.66 (2H, m), 3.08 (1H, dd, J=5, 15 Hz), 3.18 (1H, m), 3.36 (1H, m), 3.79 (1H, d, J=20 Hz), 4.05-4.09 (1H, m), 4.14 (1H, d, J=20 Hz), 4.39 (1H, m), 5.54 (1H, s), 6.64 (1H, d, J=5 Hz), 6.69-6.72 (2H, m), 6.78 (2H, m), 7.01 (1H, m). MS (ESI) (M+H)⁺ 517.11.

Step F (13): (4S,5S)-4-(3,5-difluorobenzyl)-5-((R)-2-benzhydryl-8-(triisopropylsilyloxy)-1,2,3,4-tetrahydroisoquinolin-3-yl)oxazolidin-2-one To a solution of (4S,5R)-4-(3,5-difluorobenzyl)-5-((R)-8-(triisopropylsilyloxy)-1,2,3,4-tetrahydroisoquinolin-3-yl)oxazolidin-2-one Step F (12), 120 mg, 0.23 mmol) in acetonitrile (2 mL) were added potassium carbonate (64 mg, 0.46 mmol) and bromodiphenylmethane (91 mg, 0.37 mmol). This mixture was put on microwave at 75° C. for 2 h and 15 min. Solvent was removed and the crude mixture was purified by silica gel Flash Chromatography to give 120 mg of the title compound (75% yield): ¹H NMR (CDCl₃, 500 MHz) δ 0.90 (18H, m), 1.06 (3H, m), 2.47 (1H, m), 2.76 (1H, d, J=20 Hz), 3.16-3.23 (2H, m), 3.69 (1H, d, J=20 Hz), 3.75 (1H, m), 4.02 (1H, m), 4.18 (1H, d, J=20 Hz), 4.72 (1H, m), 4.80 (1H, s), 4.92 (1H, s), 6.61 (1H, d, J=10 Hz), 6.76-6.80 (4H, m), 7.03-7.06 (1H, m), 7.17-7.30 (6H, m), 7.39 (4H, t, J=5 Hz). MS (ESI) (M+H)⁺ 683.31.

Step F (14): (4S,5S)-4-(3,5-difluorobenzyl)-5-((R)-2-benzhydryl-8-hydroxy-1,2,3,4-tetrahydroisoquinolin-3-yl)oxazolidin-2-one To a solution of (4S,5S)-4-(3,5-difluorobenzyl)-5-((R)-2-benzhydryl-8-(triisopropylsilyloxy)-1,2,3,4-tetrahydroisoquinolin-3-yl)oxazolidin-2-one (Step F (13), 200 mg, 0.3 mmol) in THF (5 mL) was added tetrabutylammonium fluoride (118 mg, 0.45 mmol). The mixture was stirred at rt for 1 h. Solvent was removed and the crude mixture was purified by silica gel Flash Chromatography to give 95 mg of the title compound (60% yield): ¹H NMR (CD₃OD, 500 MHz) δ 2.51-2.56 (1H, m), 2.68 (1H, d, J=20 Hz), 3.22 (1H, dd, J=5, 20 Hz), 3.35 (1H, m), 3.53 (1H, dd, J=5, 15 Hz), 3.80 (1H, d, J=15 Hz), 4.06-4.12 (1H, m), 4.21 (1H, m), 4.80-4.83 (1H, m), 4.91 (1H, s), 6.57 (1H, d, J=10 Hz), 6.66 (1H, d, J=5 Hz), 6.84-6.88 (3H, m), 6.98-7.01 (1H, m), 7.22 (2H, dd, J=10, Hz), 7.28-7.34 (4H, m), 7.46-7.50 (4H, m). MS (ESI) (M−H)⁻ 525.17.

Step F (15): (4S,5S)-4-(3,5-difluorobenzyl)-5-((R)-8-(allyloxy)-2-benzhydryl-1,2,3,4-tetrahydroisoquinolin-3-yl)oxazolidin-2-one To a solution of (4S,5S)-4-(3,5-difluorobenzyl)-5-((R)-2-benzhydryl-8-hydroxy-1,2,3,4-tetrahydroisoquinolin-3-yl)oxazolidin-2-one (Step F (14), 40 mg, 0.076 mmol) in DMF (2 mL) were added potassium carbonate (52 mg, 0.38 mmol) and allyl bromide (73 mg, 0.61 mmol). The mixture was stirred at rt overnight. Ethyl acetate (100 mL) was added and the mixture was washed with $H_2O$ (70 mL) twice, and dried over $Na_2SO_4$, and concentrated under vacuum to give the title compound: ¹H NMR (CDCl₃, 500 MHz) δ 2.50 (1H, m), 2.76 (1H, d, J=15 Hz), 2.90 (1H, d, J=35 Hz), 3.19 (1H, m), 3.26 (1H, dd, J=5, 10 Hz), 3.75 (1H, d, J=20 Hz), 3.80 (1H, m), 4.00 (1H, m), 4.13 (1H, d, J=20 Hz), 4.40 (2H, m), 4.72 (1H, dd, J=5, 10 Hz), 4.83 (1H, s), 4.87 (1H, s), 5.12-5.17 (2H, m), 5.84 (1H, m), 6.65 (1H, d, J=10 Hz), 6.75-6.80 (4H, m), 7.13-7.16 (1H, m), 7.19-7.32 (6H, m), 7.36 (2H, d, J=5 Hz), 7.42 (2H, d, J=5 Hz). MS (ESI) (M+H)⁺ 567.19.

Step F (16): (1S,2S)-1-((R)-8-(allyloxy)-2-benzhydryl-1,2,3,4-tetrahydroisoquinolin-3-yl)-2-amino-3-(3,5-difluorophenyl)propan-1-ol To a solution of (4S,5S)-4-(3,5-difluorobenzyl)-5-((R)-8-(allyloxy)-2-benzhydryl-1,2,3,4-tetrahydroisoquinolin-3-yl)oxazolidin-2-one (Step F (15), 40 mg, 0.07 mmol) in EtOH (3 mL) was added a solution of LiOH (17 mg, 0.7 mmol) in $H_2O$ (0.6 mL). This reaction mixture was stirred at 110° C. for 5 h and stirred at 80° C. overnight. Ethyl ether (50 mL) was added to the mixture and washed with 1N HCl (40 mL) twice. The aqueous phase was basified to pH 12 with 50% aqueous NaOH solution. This mixture was extracted with ethyl acetate (120 mL). The organic layer was dried ($Na_2SO_4$), and concentrated in vacuo to give 40 mg of the title compound of Preparation F. ¹H NMR (CDCl₃, 500 MHz) δ 1.87 (3H, brd s), 2.38 (1H, dd, J=10, 15 Hz), 2.79 (1H, d, J=20 Hz), 2.96-2.99 (2H, m), 3.05 (1H, dd, J=5, 15 Hz), 3.62 (1H, m), 3.66 (1H, dd, J=5, 10 Hz), 3.71 (1H, d, J=20 Hz), 4.04 (1H, d, J=15 Hz), 4.33-4.40 (2H, m), 4.77 (1H, s), 5.08-5.15 (2H, m), 5.81 (1H, m), 6.63 (1H, d, J=10 Hz), 6.71-6.75 (1H, m), 6.79 (1H, d, J=10 Hz), 6.88 (2H, m), 7.10-7.21 (5H, m), 7.28-7.31 (2H, m), 7.40 (2H, d, J=10 Hz), 7.44 (2H, d, J=5 Hz). MS (ESI) (M+H)+ 541.22.

Preparation G (S)-2-((S)-3-Butyl-2-oxopyrrolidin-1-yl)-4-phenylbutanoic acid

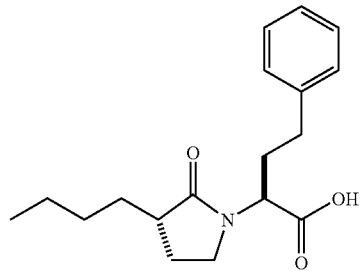

Step G (1): (4R,5S)-3-hexanoyl-4-methyl-5-phenyloxazolidin-2-one

To a solution of (4R,5S)-(+)-4-methyl-5-phenyl-2-oxazolidinone (Aldrich Chemicals, 1.77 g, 10 mmol) in THF (100 mL) at −78° C. was added nBuLi (6.6 mL, 1.6 M in Hexane, 10.6 mmol) dropwise. After 10 minutes, hexanoyl chloride (1.68 mL, 12 mmol) was added. After 30 minutes the solution was allowed to warm to rt, at which time the reaction was quenched with saturated ammonium chloride solution. After 10 minutes, 1 M NaOH was added, and the mixture extracted 3 times with ethyl acetate. The combined organic layers were dried with MgSO4, filtered, and concentrated in vacuo. Silica gel chromatography (0% to 20% EtOAc/Hexane gradient) afforded pure product (1.98 g, 72%). 1H NMR (500 MHz, CDCl3) δ ppm 0.96-0.81 (m, 6H) 1.40-1.26 (m, 4H) 1.74-1.59 (m, 2H) 3.04-2.81 (m, 2H) 4.75 (dt, J=13.8, 6.7 Hz, 1H) 5.64 (d, J=7.32 Hz, 1H) 7.44-7.23 (m, 5H).

Step G (2): (4R,5S)-3-((S)-2-allylhexanoyl)-4-methyl-5-phenyloxazolidin-2-one

To a solution of the compound of step G (1) (208 mg, 756 μmol) in THF (1.5 mL) at −78° C. was added 1 M NaHMDS (832 μL, 832 μmol) dropwise. After 10 minutes, allyl bromide (196 μL, 2.27 mmol) was added in one shot. The reaction was continued at −78° C. until TLC showed complete reaction (~6 hours). The reaction was quenched with saturated ammonium chloride solution and allowed to come to room temperature. The mixture extracted 3 times with ethyl acetate. The combined organic layers were dried with MgSO4, filtered, and concentrated in vacuo. Silica gel chromatography (0% to 10% EtOAc/Hexane gradient) afforded pure product (137 mg, 58%). 1H NMR (500 MHz, CDCl3) δ ppm 0.93-0.81 (m, 6H) 1.35-1.21 (m, 4H) 1.53-1.44 (m, 1H) 1.75-1.66 (m, 1H) 2.34-2.22 (m, 1H) 2.47-2.36 (m, 1H) 3.98-3.86 (m, 1H) 4.82-4.74 (m, 1H) 5.08-4.94 (m, 2H) 5.63 (d, J=7.32 Hz, 1H) 5.87-5.75 (m, 1H) 7.46-7.24 (m, 5H). HPLC retention time: 1.92 min (method A). MS (ESI) (M+H)+ 316.

Step G (3): (S)-2-allylhexanoic acid

To a solution of the compound of step G (2) (1.22 g, 3.86 mmol) in THF (15.6 mL) was added water (3.86 mL), and the mixture cooled to 0° C. A solution of LiOH (185.7 mg, 7.75 mmol) and 30% H2O2 (3.51 mL) in water (12.1 mL) was added, and the combined mixture stirred for 10 minutes at 0° C. The ice bath was removed, and the reaction was allowed to continue for 1 h at rt. A solution of sodium sulfite (440 mg) was added, and the reaction stirred for 10 min. Saturated sodium carbonate solution was added, and the reaction was extracted with methylene chloride. The aqueous layer was acidified to pH 1 with 6 N HCl, and extracted 3 times with diethyl ether. The combined ether layers were washed with brine, and dried over MgSO4. The extract was filtered, and concentrated in vacuo to afforded the desired product (63% yield). 1H NMR (500 MHz, CDCl3) δ ppm 0.88 (t, J=7.0 Hz, 3H) 1.22-1.41 (m, 4H) 1.43-1.57 (m, 1H) 1.57-1.73 (m, 1H) 2.18-2.31 (m, 1H) 2.32-2.53 (m, 2H) 4.97-5.14 (m, 2H) 5.65-5.87 (m, 1H) 9.85 (s, 1H).

Step G (4): (S)-ethyl 2-((S)-2-allylhexanamido)-4-phenylbutanoate

To a solution of the compound of step G (3) (421 mg, 2.69 mmol) and homophenylalanine ethyl ester hydrochloride (789 mg, 3.24 mmol) in DMF (30.1 mL) was added HATU (1.54 g, 3.24 mmol) and N-Methyl morpholine (1.24 mL, 9.42 mmol). The reaction was stirred at rt until LC showed conversion to product (<30 min). DMF was removed in vacuo, the residue suspended in water, and the product extracted 3 times to ethyl acetate. The combined organic extracts were dried over MgSO4, filtered, and concentrated in vacuo. The crude product was suspended in a minimal amount of methylene chloride and filtered through glass wool. The solution was loaded onto a silica gel column, and pure product was obtained following elution with a ethyl acetate/hexane gradient (836 mg, 90%). 1H NMR (500 MHz, CDCl3) δ ppm 0.88 (t, J=7.02 Hz, 3H) 1.19-1.38 (m, 7H) 1.40-1.50 (m, 1H) 1.57-1.69 (m, 1H) 1.92-2.06 (m, 1H) 2.08-2.26 (m, 3H) 2.28-2.41 (m, 1H) 2.52-2.75 (m, 2H) 4.18 (q, J=7.32 Hz, 2H) 4.61-4.74 (m, 1H) 4.95-5.11 (m, 2H) 5.69-5.84 (m, 1H) 5.96 (d, J=7.63 Hz, 1H) 7.10-7.34 (m, 5H). HPLC retention time: 1.76 min (method A). MS (ESI) (M+H)+ 346.

Step G (5): (S)-ethyl 2-((S)-3-butyl-2-oxopyrrolidin-1-yl)-4-phenylbutanoate

To a solution of the compound of step G (4) (400 mg, 1.16 mmol) in MeOH (23.1 mL) containing sodium acetate (69.3 mg, 856 μmol) at −78° C. was bubbled O3. TLC within 3 minutes showed complete conversion to the ozonide. Nitrogen was bubbled through the solution to remove excess O3. Triphenyl phosphine (913 mg, 3.48 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a ethyl acetate/hexane gradient. The aldehyde/hemiaminal so obtained was dissolved in methylene chloride (17.5 mL) and cooled to 0° C. Triethyl silane (5.2 mL) and TFA (5.2 mL) were simultaneously added, and the reaction stirred at 0° C. for 3 h. Solvents and reagents were removed in vacuo. Silica gel chromatography (ethyl acetate/hexane gradient) provided pure lactam ester (345 mg, 90% yield). $^1$H NMR (500 MHz, CDCl$_3$) δ ppm 0.90 (t, J=7.0 Hz, 3H) 1.24 (t, J=7.17 Hz, 3H) 1.28-1.47 (m, 5H) 1.66-1.79 (m, 1H) 1.79-1.91 (m, 1H) 1.93-2.06 (m, 1H) 2.06-2.18 (m, 1H) 2.22-2.34 (m, 1H) 2.37-2.51 (m, 1H) 2.51-2.71 (m, 2H) 3.16-3.27 (m, 1H) 3.38-3.50 (m, 1H) 4.07-4.21 (m, 2H) 4.79 (dd, J=10.83, 4.73 Hz, 1H) 7.11-7.34 (m, 5H). HPLC retention time: 1.78 min (method A). MS (ESI)(M+H)$^+$ 332.

Step G (6): (S)-2-((S)-3-butyl-2-oxopyrrolidin-1-yl)-4-phenylbutanoic acid

To a solution of the compound of step G (5) (100 mg, 302 μmol) in THF (3 mL) was added 2M LiOH (3 mL, 6 mmol). The mixture was stirred rapidly for 1 h. The mixture was made acidic with HCl, and the resulting mixture extracted 3 times with ethyl acetate. The combined organic extracts were washed with brine, dried over MgSO$_4$, filtered, and concentrated in vacuo. The pure compound of preparation G was obtained as a white powder (84 mg, 92% yield). $^1$H NMR (500 MHz, CDCl$_3$) δ ppm 0.91 (t, J=6.7 Hz, 3H) 1.28-1.41 (m, 5H) 1.66-1.78 (m, 1H) 1.79-1.92 (m, 1H) 2.00-2.21 (m, 2H) 2.27-2.38 (m, 1H) 2.38-2.49 (m, 1H) 2.54-2.73 (m, 2H) 3.20-3.32 (m, 1H) 3.35-3.47 (m, 1H) 4.68 (dd, J=10.38, 4.88 Hz, 1H) 7.12-7.34 (m, 5H). HPLC retention time: 1.63 min (method A). MS (ESI) (M+H)$^+$ 304.

Preparation H (S)-2-((S)-3-Butyl-2-oxopyrrolidin-1-yl)propanoic acid

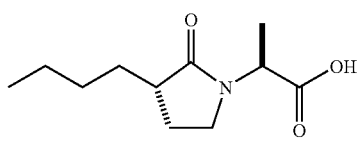

Step H (1): (S)-methyl 2-((S)-2-allylhexanamido)propanoate

To a solution of the compound of step G (3) (1.00 g, 6.41 mmol) and alanine methyl ester hydrochloride (1.07 g, 7.69 mmol) in DMF (71.5 mL) was added HATU (3.66 g, 7.70 mmol) and N-Methyl morpholine (2.95 mL, 22.4 mmol). The reaction was stirred at rt until LC showed conversion to product (<45 min). DMF was removed in vacuo, the residue suspended in water, and the product extracted 3 times to ethyl acetate. The combined organic extracts were dried over MgSO$_4$, filtered, and concentrated in vacuo. The crude product was suspended in a minimal amount of methylene chloride and filtered through glass wool. The solution was loaded onto a silica gel column, and pure product was obtained following elution with a 0-30% ethyl acetate/hexane gradient (1.23 g, 80%). $^1$H NMR (500 MHz, CDCl$_3$) δ ppm 0.87 (t, J=7.02 Hz, 3H) 1.19-1.34 (m, 4H) 1.39 (d, J=7.32 Hz, 3H) 1.41-1.50 (m, 1H) 1.57-1.66 (m, 1H) 2.06-2.23 (m, 2H) 2.29-2.40 (m, 1H) 3.74 (s, 3H) 4.55-4.66 (m, 1H) 4.95-5.09 (m, 2H) 5.68-5.82 (m, 1H) 5.97 (d, J=6.71 Hz, 1H). HPLC retention time: 1.35 min (method C). MS (ESI) (M+H)$^+$ 242.

Step H (2): (S)-methyl 2-((S)-3-butyl-2-oxopyrrolidin-1-yl)propanoate

To a solution of the compound of Step H (1) (1.23 g, 5.12 mmol) in MeOH (102 mL) containing sodium acetate (306 mg, 3.78 mmol) at −78° C. was bubbled O$_3$. TLC within 3 minutes showed complete conversion to the ozonide. Nitrogen was bubbled through the solution to remove excess O$_3$. Triphenyl phosphine (4.03 g, 15.3 mmol) was then added, and the mixture allowed to come to rt. To complete conversion of the ozonide intermediate, the solution was gently warmed at 50° C. until decomposition of the ozonide was complete. Solvents were removed in vacuo. The crude material was suspended in chloroform, filtered through glass wool onto a silica gel column, and purified via a 0% to 60% ethyl acetate/hexane gradient. The aldehyde/hemiaminal so obtained (1.26 g) was dissolved in methylene chloride (78 mL) and cooled to 0 C. Triethyl silane (23.4 mL) and TFA (23.4 mL) were simultaneously added, and the reaction stirred at 0° C. for 3 h. Solvents and reagents were removed in vacuo. Silica gel chromatography (ethyl acetate/hexane gradient) provided the lactam ester. $^1$H NMR (500 MHz, CDCl$_3$) δ ppm 0.89 (t, J=7.02 Hz, 3H) 1.26-1.47 (m, 5H) 1.43 (d, J=7.63 Hz, 3H) 1.75-1.86 (m, 2H) 2.17-2.27 (m, 1H) 2.54-2.62 (m, 1H) 3.38 (dd, J=15.72, 8.70 Hz, 1H) 3.46-3.53 (m, 1H) 3.72 (s, 3H) 4.87 (q, J=7.32 Hz, 1H). HPLC retention time: 1.28 min (method C). MS (ESI) (M+H)$^+$ 228.

Step H (3): (S)-2-((S)-3-butyl-2-oxopyrrolidin-1-yl)propanoic acid

The general procedure of step G (6) was applied to transform the compound of step H (2) into the title compound of preparation H. HPLC retention time: 1.32 min (method C). MS (ESI) (M+H)$^+$ 214.

Preparation I 1-(Butyl(methyl)carbamoyl)-1H-pyrrolo[2,3-b]pyridine-3-carboxylic acid

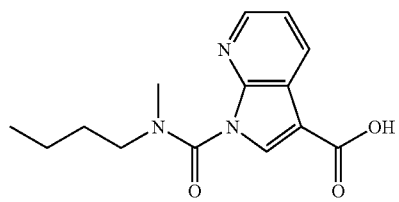

Step I (1):
N-butyl-N-methyl-1H-imidazole-1-carboxamide

Butylamine (20 g, 0.23 mol) was dissolved in 100 mL of THF and added at a quick dropwise rate to a suspension of carbonyldiimidazole (37.2 g, 0.23 mol) in 200 mL of THF. The solution was headed to reflux for 3 h, then cooled, treated with 200 mL of water, and partitioned into ethyl acetate. The organic layer was separated and then washed with brine, dried with MgSO$_4$, and then concentrated to the crude imidazolide, which was purified by distillation at 108° C. and 600 mtorr to provide a pure oil. $^1$H NMR (400 MHz, CDCl$_3$) δ ppm 7.86 (s, 1H), 7.21 (s, 1H), 7.10 (s, 1H), 3.40 (t, J=7.60 Hz, 2H), 3.06 (s, 3H), 1.61 (m, 2H), 1.31 (m, 2H), 0.93 (t, J=7.23 Hz, 3H).

Step I (2): 1H-pyrrolo[2,3-b]pyridine-3-carbaldehyde

A solution of 7-azaindolegramine (17.3 g, 0.1 mol) and hexamethylenetetramine (HMTA, 14 g, 0.1 mol) dissolved in 72 mL of 66% aqueous propionic acid was added dropwise to a refluxing solution of an additional 14 g (0.1 mol) of HMTA dissolved in 50 mL of 66% aqueous propionic acid. After addition was complete (~1 h), the solution was stirred at reflux for an additional 2 h. The heat was removed and 275 mL of water was added to the still-warm solution. The resulting homogeneous solution was stirred rapidly and placed in an ice bath. After cooling, a precipitate formed which was collected and washed with water to yield 5.80 grams of the desired aldehyde (40%). $^1$H NMR (400 MHz, CDCl$_3$) δ ppm 9.88 (s, 1H),

Step I (3): N-butyl-3-formyl-N-methyl-1H-pyrrolo[2,3-b]pyridine-1-carboxamide A solution of 9.76 g (54 mmol) of the compound from step I (1) dissolved in 100 mL of acetonitrile was treated with 11.5 g (81 mmol) of methyl iodide. The reaction solution was stirred for 16 h at rt, then concentrated to an oil. The crude imidazolium iodide was then redissolved in 70 mL of THF and 5.25 g (36 mmol) of 1H-pyrrolo[2,3-b]pyridine-3-carbaldehyde from step I (2) was added, followed by triethylamine (72 mmol, 7.2 grams). The resulting solution was heated to 60° C. for 24 h, then cooled and poured into a solution of 0.1 N HCl. Ethyl acetate was added, and the organic layer was separated, dried with brine and concentrated. The crude product (12.3 g, 132%) of the desired title compound contained an unknown impurity which was removed at the next step. MS ESI (M+H)$^+$=260.24. $^1$H NMR (500 MHz, CDCl$_3$) δ ppm 0.76-1.06 (m, 3H) 1.18-1.35 (m, 2H) 1.43-1.57 (m, 2H) 1.58-1.81 (m, 2H) 2.97-3.19 (m, 3H) 7.29-7.32 (m, 1H) 8.13 (s, 1H) 8.45 (dd, J=4.73, 1.68 Hz, 1H) 8.58 (d, J=7.94 Hz, 1H) 10.03 (s, 1H)

Step I (4): 1-(butyl(methyl)carbamoyl)-1H-pyrrolo[2,3-b]pyridine-3-carboxylic acid A solution of isobutylene in THF (50 mL, 0.1 mol) was diluted with 140 mL of THF and 270 mL of t-butanol. The crude product from step I (3) (12 g, 46 mmol) was dissolved in this solution, and then treated with a solution of 8.1 g (90 mmol) of sodium chlorite and 25 g (180 mmol) of sodium dihydrogen phosphate dissolved in 50 mL of water. The resulting reaction solution was stirred at rt for 2 h and then the volatiles were removed by rotary evaporation. The resulting aqueous solution was diluted with 0.1 N HCl until acidic and extracted with ethyl acetate. The organic layer was separated, washed with brine, and concentrated to a crude produced which was purified by crystallization from ethyl acetate hexanes to provide the purified title compound of preparation I. MS (ESI)(M-H)$^+$=274.30. $^1$H NMR (500 MHz, CDCl$_3$) δ ppm 0.93 (t, J=7.32 Hz, 3H) 1.33 (dd, J=15.11, 7.48 Hz, 2H) 1.57-1.68 (m, 2H) 3.06 (s, 3H) 3.41 (t, 2H) 7.30 (dd, J=7.93, 4.88 Hz, 1H) 8.12 (s, 1H) 8.44 (dd, J=4.58, 1.53 Hz, 1H) 8.57 (dd, J=7.93, 1.53 Hz, 1H) 10.03 (s, 1H)

Preparation J (1S,2S)-2-Amino-1-((R)-2-benzhydryl-8-methoxy-1,2,3,4-tetrahydroisoquinolin-3-yl)-3-(3,5-difluorophenyl)propan-1-ol

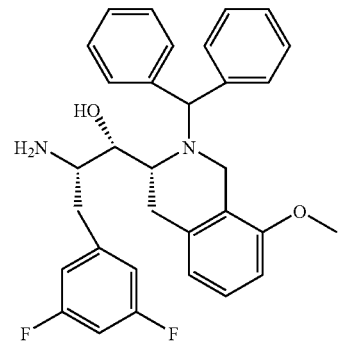

Step J (1): (4S,5S)-5-((R)-2-benzhydryl-8-methoxy-1,2,3,4-tetrahydroisoquinolin-3-yl)-4-(3,5-difluorobenzyl)oxazolidin-2-one A 60 mg (0.11 mmol) portion of (4S,5S)-4-(3,5-difluorobenzyl)-5-((R)-2-benzhydryl-8-hydroxy-1,2,3,4-tetrahydroisoquinolin-3-yl)oxazolidin-2-one from Step F (14) was dissolved in 2.5 mL of a 4:1 solution of diethyl ether and methanol. A 0.5 mL portion of 2M trimethylsilyldiazomethane was added and the solution was stirred at rt for 16 h. The excess diazomethane was quenched with the addition of several drops of acetic acid and the solvents were removed in vacuo to provide the desired product. $^1$H NMR (500 MHz, CDCl$_3$) δ ppm 2.45-2.59 (m, 1H) 3.16-3.22 (m, 1H) 3.25 (dd, J=10.07, 5.49 Hz, 1H) 3.67 (s, 3H) 3.76 (s, 1H) 3.80 (d, J=2.14 Hz, 1H) 3.83 (d, J=2.44 Hz, 1H) 3.97-4.03 (m, 1H) 4.08 (d, J=18.62 Hz, 1H) 4.70 (dd, J=10.22, 6.56 Hz, 1H) 4.85 (s, 1H) 4.92 (s, 1H) 6.66 (d, J=7.93 Hz, 1H) 6.78 (d, J=7.63 Hz, 3H) 7.14-7.19 (m, 1H) 7.20-7.29 (m, 5H) 7.32 (t, J=7.63 Hz, 2H) 7.35 (d, J=7.02 Hz, 2H) 7.42 (d, J=7.32 Hz, 2H).

Step J (2): (1S,2S)-2-amino-1-((R)-2-benzhydryl-8-methoxy-1,2,3,4-tetrahydroisoquinolin-3-yl)-3-(3,5-difluorophenyl)propan-1-ol In a manner similar to that described for the preparation of the compound of step F (16), the compound of preparation J (60 mg, 100%) was prepared from the product of step J (1). $^1$H NMR (500 MHz, CDCl$_3$) δ ppm 2.08 (s, 2H) 2.38 (dd, J=13.58, 10.83 Hz, 1H) 2.77 (d, J=17.09 Hz, 1H) 2.92-3.00 (m, 2H) 3.04 (dd, J=17.09, 5.80 Hz, 1H) 3.60 (s, 1H) 3.63 (s, 3H) 3.65-3.69 (m, 1H) 3.71 (s, 1H) 3.97 (d, J=18.31 Hz, 1H) 4.12 (q, J=7.02 Hz, 1H) 4.79 (s, 1H) 6.63 (d, J=7.93 Hz, 1H) 6.73 (dt, J=9.08, 2.17 Hz, 1H) 6.77 (d, J=7.94 Hz, 1H) 6.88 (d, J=6.10 Hz, 2H) 7.10-7.17 (m, 2H) 7.20 (t, J=7.32 Hz, 3H) 7.31 (t, J=7.63 Hz, 2H) 7.38 (d, J=7.02 Hz, 2H) 7.46 (d, J=7.32 Hz, 2H)

Example 1

(S)-2-((S)-3-Acetamido-3-((R)-sec-butyl)-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)-4-phenylbutanamide

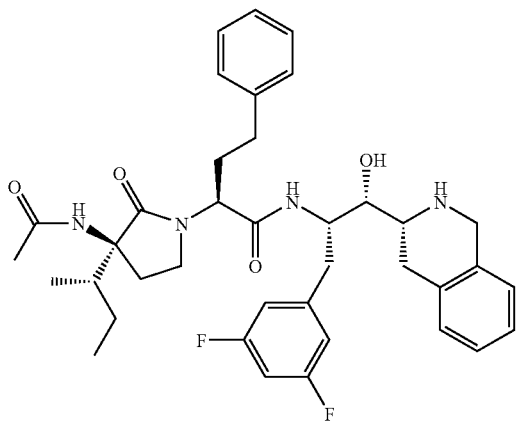

Step (A): (S)—N-((1S,2S)-1-((R)-2-(4-methoxybenzyl)-1,2,3,4-tetrahydroisoquinolin-3-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide To a solution of (S)-2-((S)-3-acetamido-3-((R)-sec-butyl)-2-oxopyrrolidin-1-yl)-4-phenylbutanoic acid (Preparation B, 25 mg, 0.069 mmol) in dichloromethane (1 mL) was added Hunig's base (27 mg, 0.21 mmol) to make a clear solution and HATU (34 mg, 0.090 mmol) was then added. After stirring for 1 h, to the reaction mixture was added (1S,2S)-1-((R)-2-(4-methoxybenzyl)-1,2,3,4-tetrahydroisoquinolin-3-yl)-2-amino-3-(3,5-difluorophenyl)propan-1-ol (Preparation A, 33.5 mg, 0.076 mmol) and the reaction mixture was stirred at rt overnight. Solvent was removed and the crude mixture was purified by silica gel Flash Chromatography to give 50 mg of the title compound: ¹H NMR (CD₃OD, 500 MHz) δ 0.68 (3H, d, J=5 Hz), 0.94-1.08 (4H, m), 1.61-1.66 (2H, m), 1.94 (3H, s), 2.01-2.20 (4H, m), 2.46 (1H, m), 2.60-2.69 (2H, m), 2.76-2.94 (2H, m), 3.00 (1H, m), 3.07 (1H, dd, J=5, 15 Hz), 3.22 (1H, m), 3.46 (1H, dt, J=5, 10 Hz), 3.62-3.69 (3H, m), 3.74 (3H, s), 3.82 (1H, m), 4.02 (1H, d, J=15 Hz), 4.14 (1H, dd, J=5, 10 Hz), 4.72 (1H, m), 6.70 (1H, m), 6.81 (2H, d, J=10 Hz), 6.87 (2H, d, J=10 Hz), 6.96 (1H, d, J=5 Hz), 7.08-7.13 (6H, m), 7.17-7.20 (2H, m), 7.24 (2H, d, J=5 Hz). MS (ESI) (M+H)⁺ 781.39.

Step (B): (S)-2-((S)-3-acetamido-3-((R)-sec-butyl)-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)-4-phenylbutanamide To a solution of (S)—N-((1S,2S)-1-((R)-2-(4-methoxybenzyl)-1,2,3,4-tetrahydroisoquinolin-3-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide (Example 1, Step (A), 50 mg) in MeOH (5 mL) was added a catalytic amount of Pd on activated charcoal (10 wt %, 15 mg) and 5 drops of acetic acid. The reaction mixture was put on hydrogenator at 55 psi overnight. The mixture was then filtered and concentrated in vacuo and purified by silica gel Flash chromatography to give 35 mg of the title compound of example 1: ¹H NMR (CD₃OD, 500 MHz) δ 0.78 (3H, d, J=5 Hz), 0.97 (3H, m), 1.04-1.10 (1H, m), 1.63-1.70 (2H, m), 1.96 (3H, s), 1.93-2.02 (1H, m), 2.09-2.14 (2H, m), 2.18-2.26 (1H, m), 2.40-2.46 (1H, m), 2.55-2.61 (1H, m), 2.76 (1H, dd, J=10, 15 Hz), 2.98 (1H, dd, J=5, 15 Hz), 3.12 (1H, m), 3.16-3.21 (1H, m), 3.27-3.34 (2H, m), 3.38-3.42 (1H, m), 4.00-4.04 (2H, m), 4.16-4.20 (1H, m), 4.24 (2H, s), 6.73 (1H, m), 6.90 (2H, d, J=5 Hz), 6.98 (2H, d, J=10 Hz), 7.09-7.19 (7H, m). MS (ESI) (M+H)⁺ 661.32

Example 2

(S)-2-((S)-3-Acetamido-3-((R)-sec-butyl)-2-oxopyrrolidin-1-yl)-N-((1R,2S)-3-(3,5-difluorophenyl)-1-hydroxy-1-((S)-1,2,3,4-tetrahydroisoquinolin-3-yl)propan-2-yl)-4-phenylbutanamide

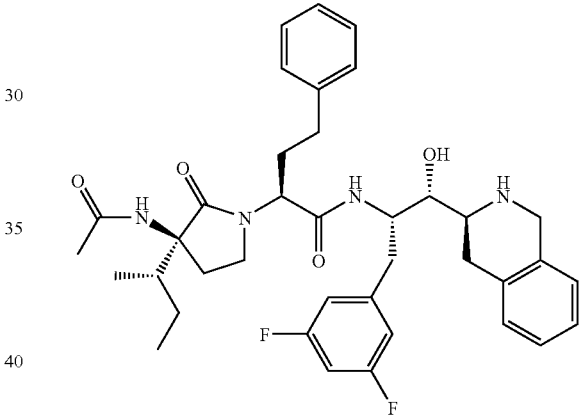

Step (A): (S)—N-((1S,2S)-1-((S)-2-(5-dibenzosuberyl)-1,2,3,4-tetrahydroisoquinolin-3-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide To a solution of (S)-2-((S)-3-acetamido-3-((R)-sec-butyl)-2-oxopyrrolidin-1-yl)-4-phenylbutanoic acid (Preparation B, 42 mg, 0.117 mmol) in dichloromethane (4 mL) was added Hunig's base (45 mg, 0.35 mmol) to make a clear solution and HATU (58 mg, 0.153 mmol) was then added. After stirring for 20 minutes, the reaction mixture was added (1S,2S)-2-amino-3-(3,5-difluorophenyl)-1-((S)-2-(5-dibenzosuberyl)-1,2,3,4-tetrahydroisoquinolin-3-yl)propan-1-ol (Preparation E, 60 mg, 0.117 mmol) and the reaction mixture was stirred at rt overnight. Solvent was removed and the crude mixture was purified by silica gel Flash Chromatography to give 50 mg of the title compound: ¹H NMR (CDCl₃, 500 MHz) δ 0.81 (3H, t, J=10 Hz), 0.95 (3H, m), 1.06-1.11 (1H, m), 1.58 (1H, m), 1.77 (1H, m), 1.88 (1H, s), 1.97 (3H, s), 2.10 (1H, m), 2.16-2.27 (3H, m), 2.34 (1H, dd, J=5, 15 Hz), 2.42 (1H, d, J=15 Hz), 2.47-2.53 (2H, m), 2.61-2.65 (1H, m), 2.86-2.95 (3H, m), 3.02 (1H, m), 3.14 (1H, m), 3.48-3.56 (2H, m), 3.69 (1H, d, J=10 Hz), 3.83-3.90 (3H, m), 4.02-4.06 (2H, m), 4.30 (1H, s), 4.67 (1H, s), 6.01 (1H, s), 6.48 (2H, d, J=5 Hz), 6.53 (1H, m), 6.78 (1H, d, J=10 Hz), 6.84 (1H, d, J=5 Hz), 6.99 (1H, m), 7.07-7.22 (14H, m). MS (ESI) (M+H)+ 853.41.

Step (B): (S)-2-((S)-3-acetamido-3-((S)-sec-butyl)-2-oxopyrrolidin-1-yl)-N-((1R,2S)-3-(3,5-difluorophenyl)-1-hydroxy-1-((S)-1,2,3,4-tetrahydroisoquinolin-3-yl)propan-2-yl)-4-phenylbutanamide A solution of (S)—N-((1S,2S)-1-((S)-2-(dibenzosuberyl)-1,2,3,4-tetrahydroisoquinolin-3-yl)-3-(3,5-difluorophenyl)-1-hydroxypropan-2-yl)-2-((S)-3-acetamido-3-((R)-sec-butyl)-2-oxopyrrolidin-1-yl)-4-phenylbutanamide (Step (A), 50 mg) in trifluoroacetic acid (3 mL) was stirred at rt for 2 h. The trifluoroacetic acid was removed with addition of toluene under vacuum. Ethyl acetate (100 mL) was added and the mixture was washed with sodium carbonate solution, H₂O, dried and concentrated under vacuum. The mixture was purified by silica gel Flash chromatography to give 20 mg of the title compound: ¹H NMR (CD₃OD, 500 MHz) δ 0.73 (3H, d, J=10 Hz), 0.96 (3H, t, J=10 Hz), 1.03-1.08 (1H, m), 1.64-1.70 (1H, m), 1.94 (3H, s), 1.98-2.04 (1H, m), 2.07-2.14 (1H, m), 2.15-2.22 (2H, m), 2.49-2.55 (1H, m), 2.64-2.79 (2H, m), 2.89-2.95 (4H, m), 3.08 (1H, q, J=5 Hz), 3.48-3.54 (2H, m), 3.59-3.64 (3H, m), 3.76 (3H, s), 3.82 (1H, d, J=15 Hz), 4.22 (1H, dt, J=5, 10 Hz), 4.28 (1H, dd, J=5, 10 Hz), 6.68 (1H, m), 6.80 (2H, d, J=5 Hz), 6.88 (2H, d, J=10 Hz), 6.96-6.97 (1H, m), 7.11-7.14 (6H, m), 7.20-7.23 (4H, m). MS (ESI) (M+H)+ 661.30.

Example 3

(S)-2-((S)-3-Acetamido-3-((R)-sec-butyl)-2-oxopyrrolidin-1-yl)-N-((1R,2S)-3-(3,5-difluorophenyl)-1-hydroxy-1-((R)-8-propoxy-1,2,3,4-tetrahydroisoquinolin-3-yl)propan-2-yl)-4-phenylbutanamide

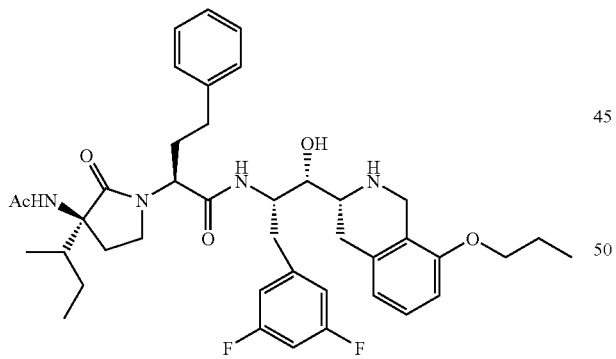

Step (A): (S)-2-((S)-3-acetamido-3-((R)-sec-butyl)-2-oxopyrrolidin-1-yl)-N-((1S,2S)-1-((R)-8-(allyloxy)-2-benzhydryl-1,2,3,4-tetrahydroisoquinolin-3-yl)-3-(3,5-difluorophenyl)-1-hydroxypropan-2-yl)-4-phenylbutanamide To a solution of (S)-2-((S)-3-acetamido-3-((R)-sec-butyl)-2-oxopyrrolidin-1-yl)-4-phenylbutanoic acid (Preparation B, 30 mg, 0.089 mmol) in dichloromethane (2 mL) was added Hunig's base (28 mg) to make a clear solution and HATU (36 mg, 0.096 mmol) was then added. After stirring for 30 min, the reaction mixture was added (1S,2S)-1-((R)-8-(allyloxy)-2-benzhydryl-1,2,3,4-tetrahydroisoquinolin-3-yl)-2-amino-3-(3,5-difluorophenyl)propan-1-ol (Preparation F, 40 mg, 0.074 mmol) and the reaction mixture was stirred at rt overnight. Solvent was removed and the crude mixture was purified by silica gel Flash Chromatography to give 50 mg of the title compound (76% yield): ¹H NMR (CDCl₃, 500 MHz) δ 0.94 (3H, d, J=10 Hz), 0.96-0.99 (3H, m), 1.14 (1H, m), 1.56 (1H, m), 1.68 (1H, s), 1.75 (1H, m), 1.98 (3H, s), 2.08 (2H, dt, J=5, 10 Hz), 2.17-2.22 (1H, m), 2.40-2.47 (2H, m), 2.59-2.66 (2H, m), 2.83-2.91 (3H, m), 2.97-3.08 (2H, m), 3.39-3.43 (2H, m), 3.87-3.91 (2H, m), 4.08 (1H, d, J=15 Hz), 4.28 (1H, dd, J=5, 10 Hz), 3.36 (1H, dd, J=5, 15 Hz), 4.73 (1H, s), 5.02-5.08 (4H, m), 5.74 (1H, m), 5.97 (1H, s), 6.55-6.60 (2H, m), 6.78 (1H, d, J=10 Hz), 7.04 (2H, d, J=5 Hz), 7.07-7.19 (8H, m), 7.23-7.29 (3H, m), 7.42 (2H, d, J=5 Hz), 7.46 (2H, d, J=5 Hz), 7.49 (1H, d, J=10 Hz). MS (ESI) (M+H)+ 883.43.

Step (B): (S)-2-((S)-3-acetamido-3-((R)-sec-butyl)-2-oxopyrrolidin-1-yl)-N-((1R,2S)-3-(3,5-difluorophenyl)-1-hydroxy-1-((R)-8-propoxy-1,2,3,4-tetrahydroisoquinolin-3-yl)propan-2-yl)-4-phenylbutanamide To a solution of (S)-2-((S)-3-acetamido-3-((R)-sec-butyl)-2-oxopyrrolidin-1-yl)-N-((1S,2S)-1-((R)-8-(allyloxy)-2-benzhydryl-1,2,3,4-tetrahydroisoquinolin-3-yl)-3-(3,5-difluorophenyl)-1-hydroxypropan-2-yl)-4-phenylbutanamide (Step 3 (A), 50 mg) in MeOH (5 mL) was added a catalytic amount of Pd on activated charcoal (10 wt %) and acetic acid (0.2 mL). The reaction mixture was put on hydrogenator at 50 psi for 3.5 h. The mixture was then filtered and concentrated in vacuo and purified by silica gel Flash chromatography to give 30 mg of the title compound of compound 3 (74% yield). ¹H NMR (CD₃OD, 500 MHz) δ 0.76 (3H, d, J=5 Hz), 0.97-1.00 (3H, m), 1.04-1.07 (4H, m), 1.64-1.69 (2H, m), 1.78-1.85 (2H, m), 1.94 (1H, s), 1.97-2.03 (4H, m), 2.06-2.20 (3H, m), 2.38-2.44 (1H, m), 2.53-2.59 (1H, m), 2.78 (1H, dd, J=10, 15 Hz), 2.96 (1H, m), 3.10-3.20 (2H, m), 3.26-3.31 (2H, m), 3.42 (1H, dt, J=5, 10 Hz), 3.97 (2H, t, J=5 Hz), 4.01-4.05 (2H, m), 4.12 (1H, m), 4.22 (1H, dt, J=5, 10 Hz), 4.32 (1H, d, J=15

Hz), 6.75 (1H, m), 6.80 (2H, d, J=10 Hz), 6.92 (2H, d, J=5 Hz), 6.95 (2H, d, J=10 Hz), 7.10-7.19 (4H, m). MS (ESI) (M+H)$^+$ 719.37.

Example 4

(S)-((1R,2S)-3-(3,5-difluorophenyl)-1-hydroxy-1-((R)-1,2,3,4-tetrahydroisoquinolin-3-yl)propan-2-yl) 2-((S)-3-butyl-2-oxopyrrolidin-1-yl)-4-phenylbutanoate

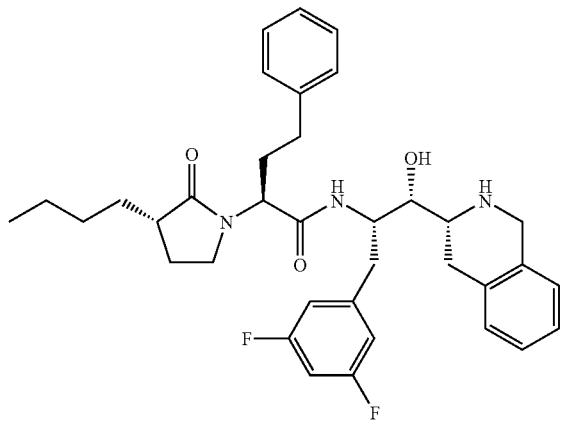

Step (A): (S)-((1R,2S)-1-((R)-2-(4-methoxybenzyl)-1,2,3,4-tetrahydroisoquinolin-3-yl)-3-(3,5-difluorophenyl)-1-hydroxypropan-2-yl) 2-((S)-3-butyl-2-oxopyrrolidin-1-yl)-4-phenylbutanoate To a solution of the compound of preparation G (39.6 mg, 131 µmol) and the compound of preparation A (47.7 mg, 109 µmol) in DMF (1.21 mL) was added HATU (62.1 mg, 131 µmol) and N-Methyl morpholine (50.0 µL, 381 µmol). The reaction was stirred at rt until LC showed conversion to product. The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (500 MHz, CDCl$_3$) δ ppm 0.89 (t, J=7.0 Hz, 3H) 1.03-1.14 (m, 1H) 1.20-1.39 (m, 5H) 1.70-1.81 (m, 1H) 1.82-1.93 (m, 1H) 1.96-2.06 (m, 1H) 2.07-2.17 (m, 1H) 2.20-2.30 (m, 1H) 2.34-2.51 (m, 2H) 2.63-2.76 (m, 1H) 2.83-3.19 (m, 5H) 3.54-3.85 (m, 6H) 3.96-4.15 (m, 1H) 4.31 (t, J=7.32 Hz, 1H) 4.54-4.72 (m, 1H) 6.56-6.87 (m, 5H) 6.94-7.32 (m, 11H). HPLC retention time: 1.91 min (method A). MS (ESI) (M+H)$^+$ 724.

Step (B): (S)-((1R,2S)-3-(3,5-difluorophenyl)-1-hydroxy-1-((R)-1,2,3,4-tetrahydroisoquinolin-3-yl)propan-2-yl) 2-((S)-3-butyl-2-oxopyrrolidin-1-yl)-4-phenylbutanoate To a solution of the compound of Step (A) in MeOH was added 10% Pd/C. The mixture was shaken under H$_2$ in a Parr shaker, and after 3 pump/flush cycles, the reaction was allowed to shake overnight. The reaction was filtered through a 0.45 µm filter, and solvents removed in vacuo. The residue was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. $^1$H NMR (500 MHz, CD$_3$OD) δ ppm 0.93 (t, J=7.02 Hz, 3H) 1.08-1.22 (m, 1H) 1.24-1.46 (m, 5H) 1.64-1.78 (m, 1H) 1.78-1.99 (m, 2H) 1.99-2.12 (m, 1H) 2.20-2.44 (m, 3H) 2.77 (m, 2H) 2.98-3.09 (m, 1H) 3.11-3.23 (m, 2H) 3.23-3.43 (m, 2H) 3.51-3.60 (m, 1H) 4.03 (dd, J=9.77, 2.14 Hz, 1H) 4.17-4.48 (m, 4H) 6.73-6.82 (m, 1H) 6.82-6.92 (m, 4H) 7.06-7.32 (m, 7H). HPLC retention time: 1.84 min (method C). MS (ESI) (M+H)$^+$ 604.

Example 5

(S)-2-((S)-3-Butyl-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)propanamide

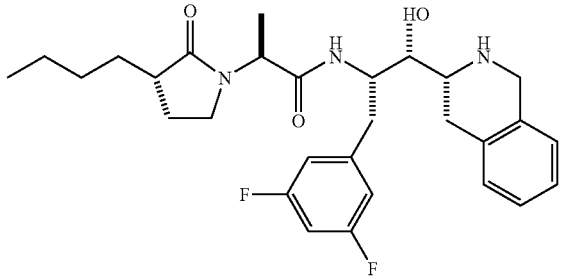

Step (A): (S)-((1R,2S)-1-((R)-2-(4-methoxybenzyl)-1,2,3,4-tetrahydroisoquinolin-3-yl)-3-(3,5-difluorophenyl)-1-hydroxypropan-2-yl) 2-((S)-3-butyl-2-oxopyrrolidin-1-yl)propanoate To a solution of the compound of preparation H (45.1 mg, 212 µmol) and the compound of preparation A (77.3 mg, 177 µmol) in DMF (2.0 mL) was added HATU (100.9 mg, 265 µmol) and N-methyl morpholine (81.3 µL, 620 µmol). The reaction was stirred at rt until LC showed conversion to product. The crude reaction mixture was injected onto a reverse-phase HPLC column (XTERRA S5 19×100 mm, gradient from 10% MeOH/H$_2$O to 90% MeOH/H$_2$O, containing 0.1% TFA) to afford, after solvent removal, pure product. HPLC retention time: 1.73 min (method C). MS (ESI) (M+H)$^+$ 634.

Step (B): (S)-2-((S)-3-Butyl-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)propanamide To a solution of the compound of step (A) in 1:1 MeOH/EtOH was added 10% Pd/C. The flask was capped with a H$_2$ balloon, and after 3 pump/flush cycles, the reaction was allowed to stir under H$_2$ overnight. The reaction was filtered through a 0.45 µm filter, and solvents removed in vacuo. Silica gel chromatography (0% to 25% MeOH/CHCl$_3$) afforded the title compound of example 5 as a pure product. $^1$H NMR (500 MHz, CD$_3$OD) δ ppm 0.93 (t, J=7.00 Hz, 3H) 1.11-1.41 (m, 9H) 1.45-1.55 (m, 1H) 1.68-1.77 (m, 1H) 2.06-2.16 (m, 1H) 2.22-2.31 (m, 1H) 2.83 (dd, J=14.04, 10.99 Hz, 1H) 3.03-3.13 (m, 2H) 3.19-3.28 (m, 2H) 3.55-3.62 (m, 1H) 4.06 (dd, J=9.80, 2.40 Hz, 1H) 4.11-4.18 (m, 1H) 4.28-4.37 (m, 2H) 4.44 (d, J=15.60 Hz, 1H) 6.75-6.82 (m, 1H) 6.87 (d, J=6.10 Hz, 2H) 7.14-7.29 (m, 4H). HPLC retention time: 1.57 min (method C). MS (ESI) (M+H)+ 514.

Example 6

(S)-2-((R)-3-Acetamido-3-isobutyl-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)-4-phenylbutanamide

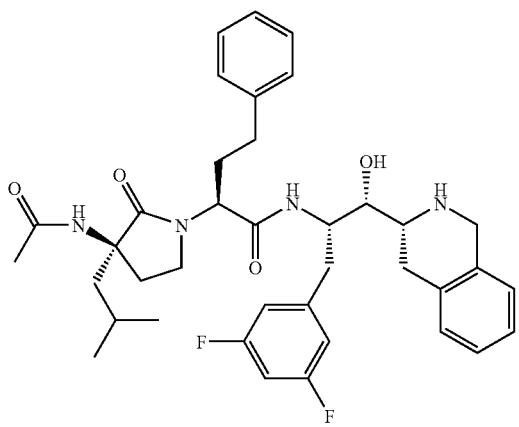

In a manner similar to the preparation of the compound of Example 1, but using Preparation B and Preparation C as starting materials, the title compound of Example 6 (5 mg) was prepared. $^1$H NMR (500 MHz, CDCl$_3$) δ ppm 1.02 (dd, J=6.56, 4.12 Hz, 6H) 1.49 (dd, J=14.50, 6.87 Hz, 1H) 1.69 (dd, J=14.34, 5.80 Hz, 1H) 1.78-1.93 (m, 1H) 1.94-2.16 (m, 5H) 2.19-2.45 (m, 4H) 2.60 (t, J=12.82 Hz, 1H) 3.06-3.23 (m, 2H) 3.23-3.33 (m, 1H) 3.35-3.56 (m, 4H) 3.88-4.19 (m, 3H) 4.25 (s, 1H) 4.40 (d, J=16.17 Hz, 1H) 6.03 (s, 1H) 6.52 (t, J=9.00 Hz, 1H) 6.81 (d, J=6.41 Hz, 2H) 7.00 (d, J=7.32 Hz, 2H) 7.03 (d, J=7.93 Hz, 1H) 7.10-7.33 (m, 5H) 8.11 (d, J=9.46 Hz, 1H) 9.17 (s, 1H) 9.50 (s, 1H)

Example 7

(2S)-2-((S)-3-Acetamido-3-sec-butyl-2-oxopyrrolidin-1-yl)-N-((1R,2S)-3-(3,5-difluorophenyl)-1-hydroxy-1-(8-methoxy-1,2,3,4-tetrahydroisoquinolin-3-yl)propan-2-yl)-4-phenylbutanamide

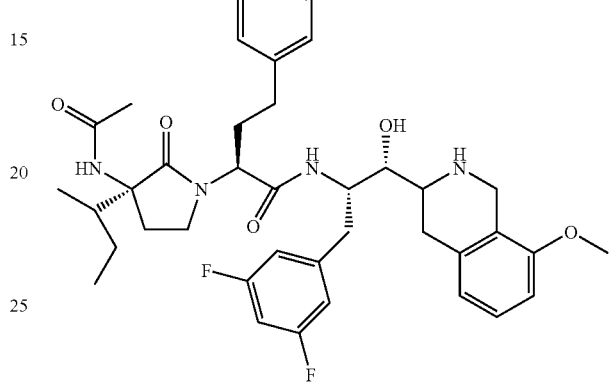

In a manner similar to the two-step procedure used for the preparation of Example 3, but using Preparation B and Preparation J as starting materials, the title compound of Example 7 (25 mg) was prepared. $^1$H NMR (500 MHz, CD$_3$OD) δ ppm 0.76 (d, J=6.71 Hz, 3H) 0.99 (t, J=7.02 Hz, 3H) 1.02-1.12 (m, 2H) 1.61-1.73 (m, 2H) 1.97 (s, 3H) 1.99 (dd, J=6.71, 3.05 Hz, 2H) 2.04-2.24 (m, 5H) 2.36-2.46 (m, 1H) 2.52-2.61 (m, 1H) 2.77 (dd, J=14.19, 10.53 Hz, 1H) 2.92-3.00 (m, 1H) 3.10 (d, J=11.90 Hz, 1H) 3.13-3.21 (m, 1H) 3.26 (dt, J=11.67, 3.32 Hz, 1H) 3.30 (d, J=3.05 Hz, 1H) 3.37-3.46 (m, 1H) 3.84 (s, 3H) 3.97-4.06 (m, 2H) 4.11 (dd, 1H) 4.17-4.26 (m, 1H) 4.29 (d, J=16.48 Hz, 1H) 6.75 (tt, J=9.16, 2.29 Hz, 1H) 6.81 (dd, J=7.78, 4.73 Hz, 2H) 6.93 (dd, J=21.52, 6.56 Hz, 4H) 7.09-7.23 (m, 4H)

Example 8

N$^1$-Butyl-N$^3$-((1R,2S)-3-(3,5-difluorophenyl)-1-hydroxy-1-(1,2,3,4-tetrahydroisoquinolin-3-yl)propan-2-yl)-N$^1$-methyl-1H-pyrrolo[2,3-b]pyridine-1,3-dicarboxamide

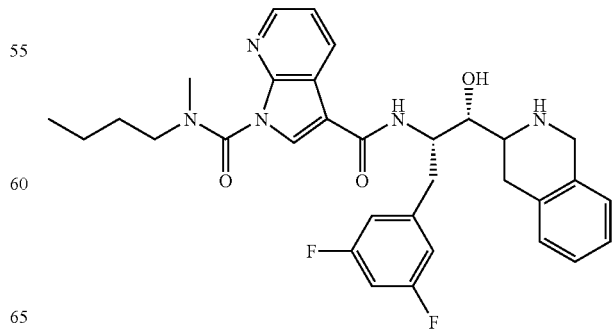

Step (A): $N^1$-butyl-$N^3$-((1S,2S)-3-(3,5-difluorophenyl)-1-hydroxy-1-(2-(4-methoxybenzyl)-1,2,3,4-tetrahydroisoquinolin-3-yl)propan-2-yl)-$N^1$-methyl-1H-pyrrolo[2,3-b]pyridine-1,3-dicarboxamide The compound of Preparation I (23 mg, 0.084 mmol) was dissolved in 1 mL of DMF and treated with DIEA (22 mg, 0.17 mmol) and HATU (42 mg, 0.11 mmol), and the resulting solution was stirred at rt for 15 min. A 37 mg (0.084 mmol) portion of the compound of Preparation A was then added and the reaction solution was stirred at rt for 16 h. The product was directly purified on reverse phase HPLC under standard conditions to provide the title compound (35 mg, 58%). $^1$H NMR (500 MHz, CD$_3$OD) δ ppm 0.90 (s, 3H) 1.12 (dd, J=21.36, 3.66 Hz, 1H) 1.32-1.46 (m, 2H) 1.66 (s, 2H) 2.88 (s, 1H) 3.02 (s, 3H) 3.31 (s, 2H) 3.38-3.55 (m, 4H) 3.66 (s, 3H) 3.84 (s, 1H) 4.14-4.33 (m, 2H) 4.32-4.53 (m, 3H) 4.62 (d, J=12.21 Hz, H) 6.70 (t, J=8.09 Hz, H) 6.80-6.98 (m, 4H) 7.07 (d, J=7.02 Hz, 1H) 7.20 (s, 1H) 7.29 (d, J=15.87 Hz, 3H) 7.40 (s, 2H) 8.08 (s, 1H) 8.27-8.42 (m, 2H).

Step (B): $N^1$-Butyl-$N^3$-((1R,2S)-3-(3,5-difluorophenyl)-1-hydroxy-1-(1,2,3,4-tetrahydroisoquinolin-3-yl)propan-2-yl)-$N^1$-methyl-1H-pyrrolo[2,3-b]pyridine-1,3-dicarboxamide A 35 mg portion of the compound from step 8 (A) was placed in a PARR flask and dissolved in 5 mL of methanol containing 30 mg of Palladium hydroxide. Hydrogen pressure to 60 psi was added and the mixture was shaken at rt for 16 h. The catalyst was removed by filtration and the resulting solution concentrated. The residue was then purified by reverse phase HPLC under standard conditions to provide 7 mg (23%) of the desired title compound of Example 8. $^1$H NMR (500 MHz, CD$_3$OD) δ ppm 0.77-1.00 (m, 3H) 1.09 (dd, J=20.91, 8.70 Hz, 2H) 1.32-1.43 (m, 2H) 1.67 (s, 2H) 2.84-2.93 (m, 1H) 2.94-3.12 (m, 2H) 3.24-3.32 (m, 3H) 3.31-3.40 (m, 2H) 3.45 (dd, J=13.89, 2.90 Hz, 2H) 3.68-3.82 (m, 1H) 4.18 (s, 1H) 4.34 (d, J=15.56 Hz, 1H) 4.36-4.45 (m, 1H) 4.44-4.53 (m, 1H) 6.73 (t, J=9.16 Hz, 1H) 6.93 (d, J=6.41 Hz, 2H) 7.14-7.18 (m, 1H) 7.19-7.23 (m, 1H) 7.23-7.29 (m, 2H) 8.04 (s, 1H) 8.21 (d, J=9.16 Hz, 1H) 8.31 (d, J=7.94 Hz, 1H) 8.33 (d, J=4.58 Hz, 1H)

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in Drosophila melanogaster S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., "Characterization of recombinant, soluble beta-secretase from an insect cell expression system." *Mol. Pharmacol.* 2001, 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 μg/ml penecillin, 10 μg/ml streptomycin, 3 μg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 μM, aprotinin 80 nM, leupeptin 2 μM, bestatin 4 μM, pepstatin A 1.5 μM, and E-64 1.4 μM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 μg/ml in assay buffer consisting of 50 mM HEPES pH 5.0 and 0.1% CHAPSO. Assays were initiated in polypropylene 96-well plates (Costar, Cambridge, Mass.) by the addition of 200 μl of cell homogenate to 50 μl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC$_{50}$ values calculated using XLfit (IDBS, Guildford, UK).

Abbreviations:
AEBSF: 4-(2-Aminoethyl)benzenesulfonyl fluoride hydrochloride
CHAPSO: 3-[(3-Cholamidopropyl)dimethylammonio]-2-hydroxy-1-propanesulfonate
D-MEM: Dulbecco's modified eagle medium
HEPES: 4-(2-Hydroxyethyl)piperazine-1-ethanesulfonic acid
RAGE™: Random Activation of Gene Expression™

The activity of specific compounds described herein and tested in the above assay is provided in Table 1.

TABLE 1

| Compound of Example | Activity Rating[a] |
|---|---|
| 1 | +++ |
| 2 | ++ |
| 3 | +++ |
| 4 | + |
| 5 | + |
| 6 | +++ |
| 7 | +++ |
| 8 | + |

[a]Activity based on $IC_{50}$ values:
+++ = <0.01 μM
++ = 0.01-1.0 μM
+ = >1.0 μM In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease, cerebral amyloid angiopathy, inclusion body myositis and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:
1. A compound of Formula (I); or a stereoisomer thereof

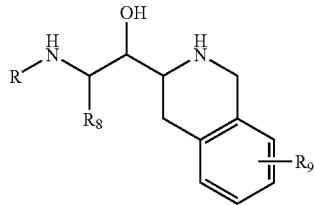

wherein
R is

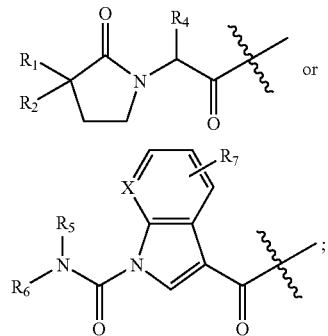

$R_1$ is hydrogen, $C_{1-6}$alkyl or $NHR_3$;

$R_2$ is $C_{1-6}$alkyl, $C_{3-6}$alkenyl, $C_{3-6}$cycloalkyl or $C_{3-6}$cycloalkyl($C_{1-4}$alkyl) in which each group is optionally substituted with a group selected from halogen, $CF_3$, $CF_2H$, OH, $OCF_3$ and $C_{1-4}$alkoxy;

$R_3$ is —C(=O)$R_{10}$, —C(=O)O$R_{10}$, —C(=O)NH$R_{10}$, —S(O)$_n$$R_{10}$ or $C_{1-6}$alkyl optionally substituted with a group selected from $C_{3-6}$cycloalkyl, halogen, $CF_3$, $OCF_3$, OH, $C_{1-4}$alkoxy and CN;

$R_4$ is $C_{1-6}$alkyl, $C_{3-6}$cycloalkyl, $C_{3-6}$cycloalkyl($C_{1-4}$alkyl), phenyl or phenyl ($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;

$R_5$ is H or $C_{1-6}$alkyl;

$R_6$ is H or $C_{1-6}$alkyl, or $R_5$ and $R_6$ together form a five or six-membered carbocyclic ring which can optionally be substituted with $C_{1-6}$alkyl or $CH_2OCH_3$;

$R_7$ is H, halogen, or $CF_3$;

$R_8$ is $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;

X is CH or N;

$R_9$ is OH, $C_{1-6}$alkoxy or $C_{1-6}$alkyl optionally substituted with halogen, OH, $CF_3$, $OCF_3$, or $C_{1-6}$ alkoxy; and $R_{10}$ is $C_{1-4}$alkyl optionally substituted with the group selected from halogen, OH, $CF_3$, $NH_2$ and $C_{1-4}$alkoxy;

or a nontoxic pharmaceutically acceptable salt thereof.

2. The compound of claim 1 of Formula (I); or a stereoisomer thereof

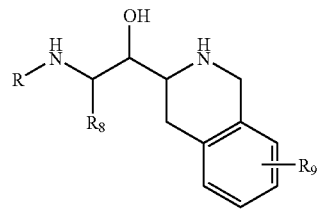

wherein
R is

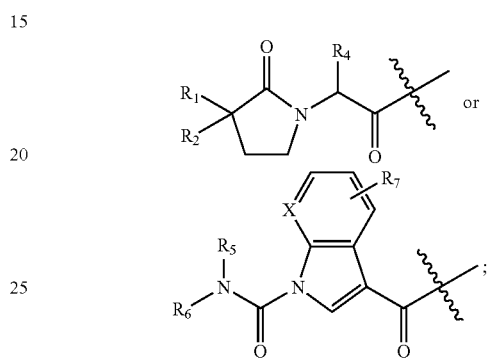

$R_1$ is hydrogen or NHC(=O)$CH_3$;

$R_2$ is $C_{1-6}$alkyl or $C_{3-6}$cycloalkyl($C_{1-4}$alkyl) in which each group is optionally substituted with a group selected from halogen, $CF_3$, $CF_2H$, OH, $OCF_3$ and $C_{1-4}$alkoxy;

$R_4$ is $C_{1-6}$alkyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;

$R_5$ is H or $C_{1-6}$alkyl;

$R_6$ is H or $C_{1-6}$alkyl, or $R_5$ and $R_6$ together form a five or six-membered carbocyclic ring which can optionally be substituted with $C_{1-6}$alkyl or $CH_2OCH_3$;

$R_7$ is H;

$R_8$ is $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;

X is CH or N; and $R_9$ is OH or $C_{1-6}$alkoxy;

or a nontoxic pharmaceutically acceptable salt thereof.

3. The compound of claim 2 of Formula (Ia); or a stereoisomer thereof:

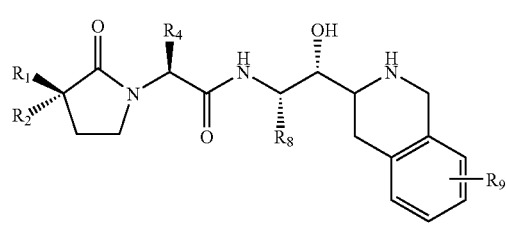

wherein
$R_1$ is hydrogen or NHC(=O)$CH_3$;
$R_2$ is $C_{1-6}$alkyl or $C_{3-6}$cycloalkyl($C_{1-4}$alkyl);

$R_4$ is $C_{1-6}$alkyl or phenyl($C_{1-4}$alkyl) in which each group is optionally substituted with the group selected from halogen, $C_{1-4}$alkyl, OH, $C_{1-4}$alkoxy, $CF_3$, $CF_2H$, $OCF_3$ and CN;

$R_8$ is $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN; and $R_9$ is OH or $C_{1-6}$alkoxy;

or a nontoxic pharmaceutically acceptable salt thereof.

4. The compound of claim 3 of Formula (Ia); or a stereoisomer thereof:

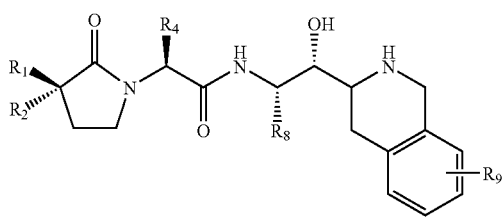

Ia wherein $R_1$ is hydrogen or NHC(=O)CH$_3$;

$R_2$ is $C_{1-6}$alkyl or $C_{3-6}$cycloalkyl($C_{1-4}$alkyl);

$R_4$ is $C_{1-6}$alkyl or phenyl($C_{1-4}$alkyl);

$R_8$ is benzyl optionally substituted with one to two halogen groups; and $R_9$ is OH or $C_{1-6}$alkoxy;

or a nontoxic pharmaceutically acceptable salt thereof.

5. The compound of claim 1 selected from the group consisting of:

(S)-2-((S)-3-Acetamido-3-((R)-sec-butyl)-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)-4-phenylbutanamide;

(S)-2-((S)-3-Acetamido-3-((R)-sec-butyl)-2-oxopyrrolidin-1-yl)-N-((1R,2S)-3-(3,5-difluorophenyl)-1-hydroxy-1-((S)-1,2,3,4-tetrahydroisoquinolin-3-yl)propan-2-yl)-4-phenylbutanamide;

(S)-2-((S)-3-Acetamido-3-((R)-sec-butyl)-2-oxopyrrolidin-1-yl)-N-((1R,2S)-3-(3,5-difluorophenyl)-1-hydroxy-1-((R)-8-propoxy-1,2,3,4-tetrahydroisoquinolin-3-yl)propan-2-yl)-4-phenylbutanamide;

(S)-((1R,2S)-3-(3,5-difluorophenyl)-1-hydroxy-1-((R)-1,2,3,4-tetrahydroisoquinolin-3-yl)propan-2-yl) 2-((S)-3-butyl-2-oxopyrrolidin-1-yl)-4-phenylbutanoate;

(S)-2-((S)-3-Butyl-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)propanamide;

(S)-2-((R)-3-Acetamido-3-isobutyl-2-oxopyrrolidin-1-yl)-N-((1R,2S)-3-(3,5-difluorophenyl)-1-hydroxy-1-((R)-1,2,3,4-tetrahydroisoquinolin-3-yl)propan-2-yl)-4-phenylbutanamide;

(2S)-2-((S)-3-Acetamido-3-sec-butyl-2-oxopyrrolidin-1-yl)-N-((1R,2S)-3-(3,5-difluorophenyl)-1-hydroxy-1-(8-methoxy-1,2,3,4-tetrahydroisoquinolin-3-yl)propan-2-yl)-4-phenylbutanamide; and $N^1$-Butyl-$N^3$-((1R,2S)-3-(3,5-difluorophenyl)-1-hydroxy-1-(1,2,3,4-tetrahydroisoquinolin-3-yl)propan-2-yl)-$N^1$-methyl-1H-pyrrolo[2,3-b]pyridine-1,3-dicarboxamide;

or a nontoxic pharmaceutically acceptable salt thereof.

6. A pharmaceutical composition comprising a therapeutically effective amount of a compound of claim 1 in association with a pharmaceutically acceptable carrier or diluent.

7. A method for the treatment of Alzheimer's Disease, cerebral amyloid angiopathy or Down's Syndrome, which comprises administering to a mammal in need thereof a therapeutically effective amount of a compound of claim 1.

* * * * *